US012346829B2

(12) United States Patent
Adib et al.

(10) Patent No.: US 12,346,829 B2
(45) Date of Patent: Jul. 1, 2025

(54) DYNAMIC MODEL SELECTION AND RULE BASED DATA INTERPRETATION

(71) Applicant: Biocogniv Inc., Burlington, VT (US)

(72) Inventors: Artur Borges Adib, South Burlington, VT (US); Steven Andrew Wallace, Hinesburg, VT (US)

(73) Assignee: Biocogniv Inc., Burlington, VT (US)

( * ) Notice: Subject to any disclaimer, the term of this patent is extended or adjusted under 35 U.S.C. 154(b) by 945 days.

(21) Appl. No.: 17/388,002

(22) Filed: Jul. 28, 2021

(65) Prior Publication Data

US 2023/0030064 A1 Feb. 2, 2023

(51) Int. Cl.
| | |
|---|---|
| G06N 5/025 | (2023.01) |
| G01N 33/487 | (2006.01) |
| G06F 18/214 | (2023.01) |
| G06N 5/022 | (2023.01) |
| G16H 10/40 | (2018.01) |
| G16H 10/60 | (2018.01) |

(52) U.S. Cl.
CPC ....... *G06N 5/025* (2013.01); *G01N 33/48771* (2013.01); *G06F 18/214* (2023.01); *G06N 5/022* (2013.01); *G16H 10/40* (2018.01); G16H 10/60 (2018.01)

(58) Field of Classification Search
CPC .......... G06N 5/025; G06N 5/022; G06N 5/01; G01N 33/48771; G06F 18/214; G06F 18/285; G16H 10/40; G16H 10/60; G16H 40/20; G16H 50/20
See application file for complete search history.

(56) References Cited

U.S. PATENT DOCUMENTS

| | | | | |
|---|---|---|---|---|
| 2010/0241443 | A1* | 9/2010 | Becker | G06Q 10/06 715/764 |
| 2011/0161113 | A1* | 6/2011 | Rumak | G06Q 10/10 705/3 |
| 2015/0148919 | A1* | 5/2015 | Watson | G06N 5/043 700/31 |
| 2015/0331995 | A1* | 11/2015 | Zhao | G16H 50/20 705/2 |
| 2017/0235909 | A1* | 8/2017 | Lozano | G16H 40/20 705/3 |
| 2019/0051420 | A1* | 2/2019 | Zhao | G16Z 99/00 |
| 2019/0108898 | A1* | 4/2019 | Gulati | G16H 10/60 |

(Continued)

*Primary Examiner* — Jordany Nunez
(74) *Attorney, Agent, or Firm* — Cognition IP, P.C.; Edward Steakley

(57) ABSTRACT

Methods, systems, and apparatus, including computer programs encoded on computer storage media for dynamic model selection and rule based data interpretation. The system receives a plurality of data sets from one or more external computing systems, each of the data sets including multiple data fields including one or more code values and data values for one or more medical tests. The system provides a plurality of medical test processing models wherein each medical test processing model includes a data interpretation rule structure for processing different types of the medical tests. The system selects a particular medical test processing model based on the one or more code values of the medical test. The system uses the selected medical test processing model to process the data values of the one or more medical tests to generate an interpreted medical test data set.

22 Claims, 20 Drawing Sheets

(56) References Cited

U.S. PATENT DOCUMENTS

| | | | | |
|---|---|---|---|---|
| 2019/0156947 | A1* | 5/2019 | Nakamura | G16H 50/20 |
| 2020/0160980 | A1* | 5/2020 | Lyman | G06N 3/045 |
| 2020/0334416 | A1* | 10/2020 | Vianu | G06V 10/764 |
| 2023/0004785 | A1* | 1/2023 | Uehara | G06N 3/098 |

* cited by examiner

PRODUCT DEFINITION INFO

ID: 2d3d666cb-b75b-448d-9e38-5c65a566af53 ⟵ 611
TYPE: COVID_INTERP
MIN PATIENT AGE: 0
MAX PATIENT AGE: 150
UPDATE

INPUT FIELDS

New | Edit

| CODE ▲ | NAME | VALUE TYPE ⇕ | MAX VALUE ⇕ | MIN VALUE ⇕ |
|---|---|---|---|---|
| igg | IGG Test History | STRING | | |
| igm | IGM Test History | STRING | | |
| pcr | PCR Test History | STRING | | |

612 ⟶ (points to MIN VALUE)

Showing 1 to 3 of 3 entries    Search: [   ]    Previous [1] Next

COMPUTED RESULTS

| CODE | NAME | VALUE TYPE | MAX VALUE | MIN VALUE |
|---|---|---|---|---|
| interpOutput | | | | |

613

Showing 1 to 1 of 1 entries    Search: [   ]    Previous [1] Next

COMMON ACTIONS

Reset input fields and output results to the pre-defined field sets
Reset the data warehouse schema to match the defined inputs and outputs

[ SET DEFAULT VALUES ]
[ UPDATE DATA WAREHOUSE SCHEMA ]

Sidebar:
AI COVID
  Calculator
  Timings
PRODUCT DEFINITIONS
  Search
DATA PROVIDERS
  Configurations Search
  Order Results Search
  Redox
CLIENTS
  Search
COLLECTORS
  Search
JOBS
  Queue
ADMINISTRATION
  Feature Switches
  Test Email

AI COVID
Calculator
Timings

PRODUCT DEFINITIONS
Search

DATA PROVIDERS
Configurations Search
Order Results Search
Redox

CLIENTS
Search

COLLECTORS
Search

JOBS
Queue

ADMINISTRATION
Feature Switches
Test Email

← 620

CLIENTS

[New] [Edit]

Search: [      ]

| ID | NAME ⇕ | PATIENT LOOKUP | ALLOWS GENERATED TEST DATA | COLLECTOR TTL DAYS ⇕ | INPUTS TTL DAYS ⇕ |
|---|---|---|---|---|---|
| b452384a-6ffb-44d0-a701-de01a843dd78 | UTMB-UNIT-TEST / 621 | MR,MRN | true | 180 | |

| ID | NAME | PATIENT LOOKUP | ALLOWS GENERATED TEST DATA | COLLECTOR TTL DAYS | INPUTS TTL DAYS |
|---|---|---|---|---|---|

Showing 1 to 1 of 1 entries

Previous [1] Next

FIG. 6C

CLIENT INFO

ID: b4523844-6ffb-44d0-a701-de01a843dd78 — 631
NAME: AMB-UNIT-TEST
PATIENT LOOKUP: MR,MRN
ALLOWS GENERATED TEST DATA: ☑

PRODUCT INSTALLATIONS

[New] [Edit]                                                                                              Search: [       ]

| ID ⇕ | STATUS ⇕ | TRIGGER ORDER CODE ⇕ | PRODUCT DEFINITION ⇕ | DATA PROVIDER ⇕ | PROV EVENT SOURCES ⇕ | PROV RESULTS DESTINATION ⇕ | MODEL VERSION |
|---|---|---|---|---|---|---|---|
| 5588661f-c5a6-4efe-9a95-f0881e07946b | ENABLED | 80000101439 | COVID INTERP | REDOX [ENABLED] | 42217ee4-b9a8-4ee1-bba4-d71713464711 | 8316ab20-a0ee-4182-afe4-c0505758b6ac | 1 |

Showing 1 to 1 of 1 entries — 632                                                          Previous [1] Next

DATA PROVIDER ORDER RESULTS — 633

Search: [       ]

| ID ▲ | CLIENT ⇕ | DATA PROVIDER ⇕ | DATA PROVIDER EVENT ⇕ | PROV RESULT DESTINATION | DATA PROVIDER ORDER CODE | MODEL VERSION CREATED AT ⇕ |
|---|---|---|---|---|---|---|
| 485f3c8a-ba51-4824-a417-79600815b4c8 | AMB-UNIT-TEST | REDOX | a3faecf3-2ee2-4ac2-8f25-0e479eefe580 | | COV19QUALM | 2021-07-01T14:59:41Z |
| 5e754ff2-b385-4179-9544-da431227cefe | AMB-UNIT-TEST | REDOX | 02a9fe46-5215-4113-86c2-1dbcb6521377 | | COV19QUALG | 2021-06-29T21:22:16Z |
| e28123da-a9c2-431e-8124-e4ec66b758df | AMB-UNIT-TEST | REDOX | 097d04e0-ea56-4052-8487-dce0064a28b6d | | COVID19R | 2021-06-29T21:00:16Z |
| 5c4b8666-4236-4e81-8552-8534f26f57c7 | AMB-UNIT-TEST | REDOX | 6bca14a2-4e9c-4c2d-978c-63c9356e3b15 | | COV19QUALM | 2021-06-29T20:49:11Z |
| 95479737-8842-417e-a46d-a6f2e9e9868b | AMB-UNIT-TEST | REDOX | b716be3d-b0ac-4a61-935e-7eb2b0d8b7df | | COV19QUALM | 2021-06-29T20:48:11Z |
| a603cc72-0347-472b-8040-341cf7f60f3f | AMB-UNIT-TEST | REDOX | 4acd47f-77a6-49a3-85c9-03bafc50c620 | | COV19QUALG | 2021-06-29T20:45:56Z |
| 3efc5a03-b420-4731-b4c0-0718f12b18a6d | AMB-UNIT-TEST | REDOX | fe93a626-7e4d-45d3-bcbf-e04be5208c94 | | COV19QUALG | 2021-06-29T19:10:46Z |
| ff9d1252-05cc-4684-b6d6-7a4b5a71acd1 | AMB-UNIT-TEST | REDOX | f9d5342a-9359-456a-8815-5cf3c885235b | | COVID19 | 2021-06-29T19:01:36Z |
| d090a2e1-014b-443f-96df-2a10c9a5d09e | AMB-UNIT-TEST | REDOX | c367407a-9e0b-4770-bd71-d62da6ed9008 | | COVID19 | 2021-06-29T18:46:06Z |
| 4f46edf1-5811-44ad-88e2-c3e813a2feaa | AMB-UNIT-TEST | REDOX | d0e11969-b983-4768-8a1e-91a258161510 | | COVID19 | 2021-06-29T18:44:06Z |

FIG. 6D

REPORT 645

Choose File | No file chosen    IMPORT CONFIG

GENERATE REPORT

WARNINGS
◎ Installation Valid

FIELD MAPPING
New | Copy | Edit | Delete

| ID | PRODUCT FIELD CODE | SOURCE TYPE | INSTALLATION ORDER CODE | INSTALLATION RESULT CODE | INSTALLATION UNITS | REQUIRED TO COMPUTE | EXPRESSION | NORMALIZATION EXPRESSION |
|---|---|---|---|---|---|---|---|---|
| b52b097bd-7239-441c-b71c-9e3113bf3a57 | igg | LAB_RESULT | COV19QUALG | 8000012393 | | false | SUBSTITUTE (igg,"OK", "Good") | SUBSTITUTE(SUBSTITUTE(datain, "Presumptive Positive","Positive"), "Not Detected","Negative") |
| 843abf28-2452-4f8b-bd41-909d443ca442 | igm | LAB_RESULT | COV19QUALM | 8000012464 | | false | | SUBSTITUTE(SUBSTITUTE(datain, "Presumptive Positive","Positive"), "Not Detected","Negative") |
| 49bda700-a6a1-49c4-9b64-9f33a73dd497 | pcr | LAB_RESULT | COVID19 | 8000012381 | | false | | SUBSTITUTE(SUBSTITUTE(datain, "Presumptive Positive","Positive"), "Not Detected","Negative") |
| 6365af57-b7af-4a97-a558-ee29ee8eb655 | pcr | LAB_RESULT | COVID19 | 8000012384 | | false | | SUBSTITUTE(SUBSTITUTE(datain, "Presumptive Positive","Positive"), "Not Detected","Negative") |
| 34b52c3c-4246-414b-b61d-5f6108b6eb3 | pcr | LAB_RESULT | COVID19 | 8000012385 | | false | | SUBSTITUTE(SUBSTITUTE(datain, "Presumptive Positive","Positive"), "Not Detected","Negative") |
| 1b71fb1d-5fd0-4d8a-abd5-8ffa340ca95c | pcr | LAB_RESULT | COVID19R | 8000012386 | | false | | SUBSTITUTE(SUBSTITUTE(datain, "Presumptive Positive","Positive"), "Not Detected","Negative") |
| 5f594ec7-0ee1-4029-88b9-e3115da4b6ad3 | pcr | LAB_RESULT | COVID19 | 8000101427 | | false | | SUBSTITUTE(SUBSTITUTE(datain, "Presumptive Positive","Positive"), "Not Detected","Negative") |

646

Showing 1 to 7 of 7 entries      Previous [1] Next

RESULT MAPPING
New | Copy | Edit | Delete

| ID | PRODUCT FIELD CODE | SOURCE TYPE | PRODUCT CODE | INSTALLATION RESULT CODE | INSTALLATION UNITS | REQUIRED TO COMPUTE | EXPRESSION | NORMALIZATION EXPRESSION |
|---|---|---|---|---|---|---|---|---|
| d1cfc11f-a9cb-4210-9e23-1bc18f6f1c7e | | | interpNumber | 8000012418 | | | | |

647         PROVIDER CODE

COLLECTOR INFO

| | |
|---|---|
| ID: | 7165a872-db53-489d-8370-19267de21617 |
| STATUS: | COMPUTED |
| ORDERED AT: | 2021-07-01T14:58:00Z |
| CANCEL REASON: | |
| FAILURE METADATA: | |
| CLIENT: | b4523844-6ffb-44d0-a701-de01a843dd78 |
| PATIENT: | cd8551a8-e580-461a-8479-ce162019e6b4 |
| VISIT: | 805403 |
| INSTALLATION: | 558866lf-c5a6-4efe-9a95-f0881e07946b |
| ORDER ID: | 21H-18210001 |
| APPLICATION ORDER ID: | 1099407 |
| EXPIRE AFTER: | 2021-07-03T02:59:36.714392Z |
| DATA PROVIDER ORDER ID: | 21H-18210001   UPDATE |

MAPPED RESULT DATA — 661

662 Search: [ ]

| PRODUCT CODE ▲ | VALUE ⇔ | SOURCE SERIES | RESULTED AT ⇔ | VALUE STATUS ⇔ | FAILURE REASON ⇔ | LAST EVENT ID |
|---|---|---|---|---|---|---|
| igg | | | 1970-01-01T00:00:00Z | WAITING | | |
| igm | Negative | | 2021-07-01T14:58:00Z | VALID | | a3faecf3-2ee2-4ac2-8t25-0e479eefe580 |
| pcr | | | 1970-01-01T00:00:00Z | WAITING | | |

| PRODUCT CODE | VALUE | EVENT | RESULTED AT | SOURCE SERIES | VALUE | VALUE TYPE | DATA PROVIDER ORDER ID | FAILURE REASON | LAST EVENT ID |
|---|---|---|---|---|---|---|---|---|---|
| | | | | | | | 21H-18210001   UPDATE | | |

Showing 1 to 3 of 3 entries

| CODE | EVENT | VALUE | | | |
|---|---|---|---|---|---|
| pcr | | | | | |
| igm | a3faecf3-2ee2-4ac2-8t25-0e479eefe580 | Negative | STRING | | |
| igg | | | | | |

663

COMPUTED DATA

CREATE COMPUTE IF READY JOB

| CODE | EVENT | VALUE | VALUE TYPE |
|---|---|---|---|
| interpOutput | | comment_75_interp | STRING |

664

---

AI COVID
 Calculator
 Timings
PRODUCT DEFINITIONS
 Search
DATA PROVIDERS
 Configuration Search
 Order Results Search
 Redox
CLIENTS
 Search
COLLECTORS
 Search
JOBS
 Queue
ADMINISTRATION
 Feature Switches
 Test Email

700

```
┌─────────────────────────────────────────────────┐
│ Provide a rules engine comprising multiple      │
│ interpretation rules used to analyze the data   │──── 702
│ values of the one or more values of a medical   │
│ test, the interpretation rule including         │
│ lookup data values                              │
└─────────────────────────────────────────────────┘
                        │
                        ▼
┌─────────────────────────────────────────────────┐
│ Select an interpretation rule based on the data │──── 704
│ values of the medical test and the lookup data  │
│ values                                          │
└─────────────────────────────────────────────────┘
                        │
                        ▼
┌─────────────────────────────────────────────────┐
│ Generate an output of the interpretation text   │
│ where the interpretation rule includes lookup   │──── 706
│ data values of the medical test corresponding   │
│ to data value criterion of the interpretation   │
│ rule                                            │
└─────────────────────────────────────────────────┘
```

FIG. 7

|  | Medical Test A | Medical Test B | Medical Test C | Output |
| --- | --- | --- | --- | --- |
| Interp. Rule 1 | Positive | 214 - 470 | < 3.0 | Output 1 |
| Interp. Rule 2 | Negative | 214 - 470 | < 3.0 | Output 5 |
| Interp. Rule 3 | Positive | > 470 | < 3.0 | Output 3 |

910

Real-world example: Coags

| | |
|---|---|
| PT | 12.0- 14.7 Sec.    14.3 |
| INR | 1.1 |
| aPTT | 26 - 36 Sec.    30 |
| Fibrinogen | 214 - 470    487 |
| Platelet | 135 - 361 10*3µ/L    433 ～1102 |
| von Willebrand Panel | |
| Factor VIII | 47-170%    123 |
| vWF antigen (Ag) | 52-214%    82 |
| vWF functional (RCF) | 51-215%    75    1104 |

Interpretation:
The results for the von Willebrand factor antigen test and the von Willebrand factor activity test are both in the normal range. Von Willebrand factor is known to be an acute phase reactant, and therefore elevated vWF values are commonly observed particularly in this case as fibrinogen and platelet count are elevated. When the values are elevated, the approximate elevation over baseline is 3-fold. If the patient's values are divided by 3 in this case, the level of von Willebrand factor is far below normal and would represent disease.

Recommendation:
It would be highly informative to repeat the von Willebrand factor panel when the patient does not have an acute phase stimulus because this patient may truly suffer from von Willebrand disease and have abnormal hemostasis at baseline.

FIG. 11

DYNAMIC MODEL SELECTION AND RULE BASED DATA INTERPRETATION

BACKGROUND

Medical tests can be important tools for the diagnosis and development of treatment plans for patients. However, current systems rely on manual interpretation of medical test data by a trained pathologist. Such systems suffer from low bandwidth and slow turnaround times. Moreover, the interpretation of medical test data has not been systematized. It would be desirable to automate interpretation of medical test data to improve data interpretation for patients and clinicians.

SUMMARY

In general, one innovative aspect of the subject described in this specification can be embodied in systems, computer readable media, and methods that includes operations for dynamic model selection and rule based data interpretation. One system performs the operations of receiving a plurality of data sets from one or more external computing systems, each of the data sets including multiple data fields including a source identifier, one or more code values and data values for one or more medical tests being associated with a patient identifier. The system provides a plurality of medical test processing models wherein each medical test processing model includes a data interpretation rule structure for processing different types of the medical tests. The system selects a particular medical test processing model based on the one or more code values of the medical test. The system uses the selected medical test processing model to process the data values of the one or more medical tests to generate an interpreted medical test data set, the interpreted data set including the source identifier, the one or more code values and data values for the one or more medical tests, and a set of interpretation text based on the medical test data values. The system transmits the interpreted medical test data set to an external computing system, wherein the external computing system is selected based on the source identifier.

In another aspect of the system, the system determines that a medical test processing model is valid for the age of the patient.

In another aspect of the system, the system selects a medical test processing model for a particular medical test, wherein a different model is applicable based on the age of the patient.

In another aspect of the system, the system provides a rules engine comprising multiple interpretation rules used to analyze the data values of the one or more values of a medical test, the interpretation rules including lookup data values. The system selects an interpretation rule based on the data values of the medical test and the lookup data values. The system generates an output of interpretation text where the interpretation rule includes lookup data values of the medical test corresponding to data value criterion of the interpretation rule.

In another aspect of the system, the data values for the medical test include only a value of either a positive or a negative test result.

In another aspect of the system, the data values for the medical test include two values, the first value being either a positive or a negative test result, and the second value being either a positive or a negative test result.

In another aspect of the system, the system receives an order from the one or more external computer systems and creating, by a collector system, a collector. The collector asynchronously waits to receive one or more data values for the one or more medical tests from the one or more external computer systems. In response to receiving a plurality of events from the one or more external computer systems, the system evaluates the events to determine a subset of events that match an order identifier and patient identifier of the collector. The system stores one or more data values for the one or more medical tests from the subset of events and analyzes the data values to determine that a required subset of data values is received. When the required subset of data values is received, the system uses the selected medical test processing model to process the data values of the one or more medical tests from the subset of events to generate an interpreted medical test data set.

In another aspect of the system, after generating an interpreted medical test data set, the collector asynchronously waits for new data values for additional medical tests. The system iteratively generates new interpreted medical test data sets when new data values for additional medical tests are received by using the selected medical test processing model to process the new data values.

In another aspect of the system, the system provides a configuration mapping comprising a plurality of mappings from a first set of code values for the one or more medical tests, the first set of code values from the external computing systems, to a second set of code values for the one or more medical tests, the second set of code values for the interpretation rules. Prior to applying the interpretation rule, the system applies the configuration mapping to map the code values of the one or more medical tests of the data sets into the second set of code values.

In another aspect of the system, the system provides a model user interface for configuring one or more medical test processing models, the model user interface including user interface elements for adding one or more medical tests and data values to a medical test processing model. The system provides a model installation user interface for configuring one or more configuration mappings, the model installation user interface including user interface elements for editing mapped code values of the one or more configuration mappings.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein:

FIG. 6B illustrates an exemplary user interface for viewing a medical test processing model definition.

FIG. 6C illustrates an exemplary user interface for viewing clients.

FIG. 6D illustrates an exemplary user interface for viewing client information.

FIG. 6F illustrates an exemplary user interface that is a continuation of an exemplary user interface for viewing product installation information.

FIG. 6H illustrates an exemplary user interface for viewing collector information.

FIG. 7 is a flow chart illustrating an exemplary method for a rules engine generating an output interpretation text.

FIG. 11 illustrates an exemplary generated interpretation text.

DETAILED DESCRIPTION

Figure 1:
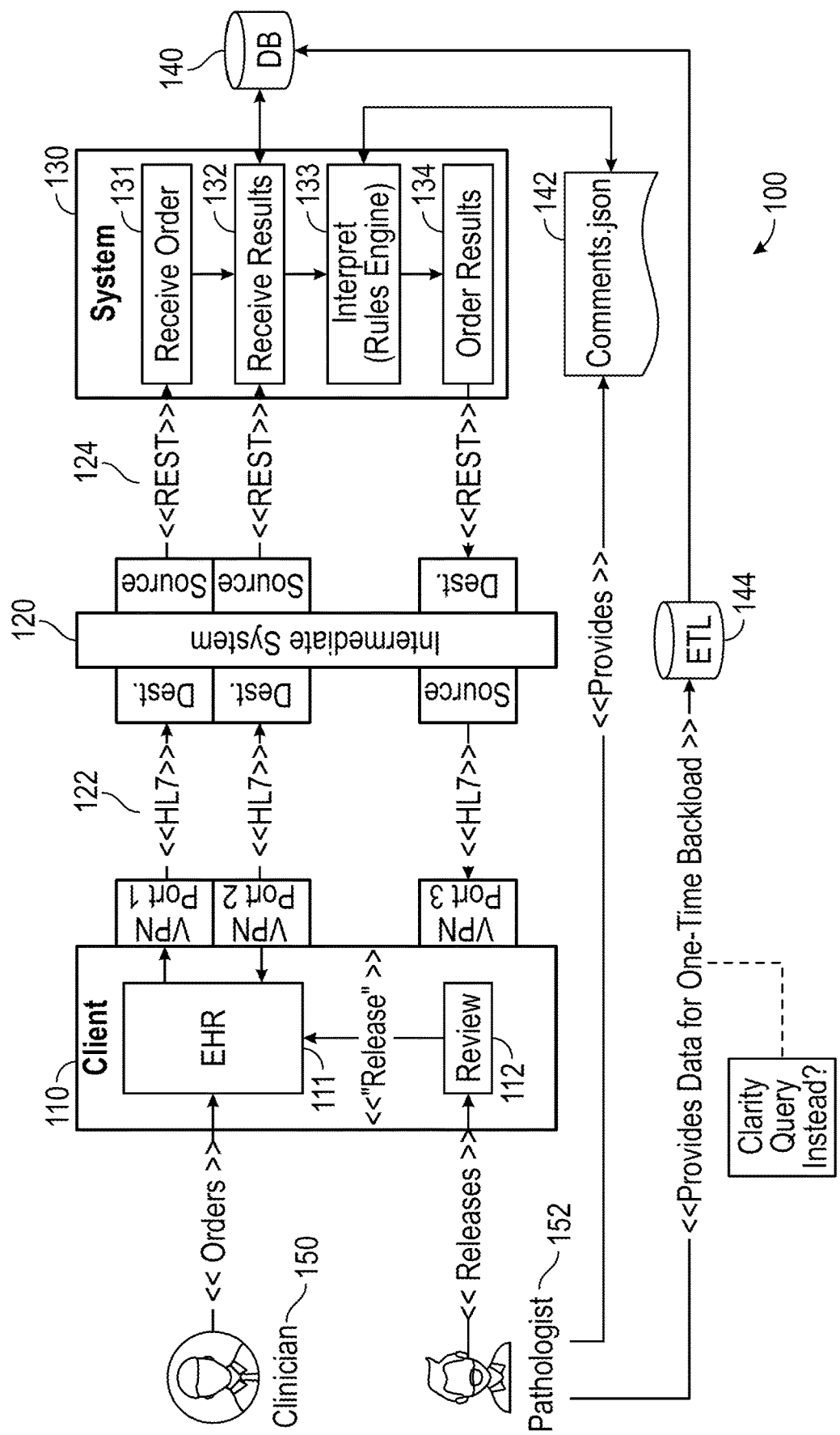
FIG. 1 illustrates an exemplary environment 100 in which embodiments for dynamic model selection and rule based data interpretation may be performed.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

FIG. 1 illustrates an exemplary environment 100 in which embodiments for dynamic model selection and rule based data interpretation may be performed. Clinician 150 may manage patient records through electronic health records (EHR) system 111. The EHR 111 may include a digital version of patient medical charts that are maintained by a medical provider for a plurality of patients. For example, EHR 111 may include for each patient the patient's medical history, diagnoses, medications, treatment plans, medical test results, medical imaging, and so on. Clinician 150 may review and enter information into the EHR 111 in response to, or when, seeing patients in order to assist with treatment. Client 110 may comprise an institution, such as a hospital, medical provider, medical practice, urgent care, and so on. Client 110 may employ clinician 150 and provide and host the computer system of the EHR 111.

In some embodiments, clinician 150 may enter an order for an interpretation of medical test data into the EHR 111. The order may specify the type of interpretation desired and optionally medical test data to be interpreted. The order may be for diagnosis, development of a patient treatment plan, and so forth. The EHR 111 transmits the order through virtual private network (VPN) connection 122 to intermediary system 120. The intermediary system 120 interfaces with a plurality of different EHRs that are used by a plurality of different clients and maps the orders and events from the different EHRs into a canonical format that may be used by system 130. For example, two different EHRs may each code orders in a different format specific to that EHR, and the intermediary system 120 maps the two different codes into an identical format (if they are for the same type of order) for consumption by the system 130. Similarly, two different EHRs may code medical test data in different formats specific to that EHR, and the intermediary system 120 maps the two different codes into an identical format (if the underlying medical test data is the same) for consumption by the system 130.

After mapping the order into the canonical format, the intermediary system 120 transmits the order over a representational state transfer application programming interface (REST API) 124 to system 130. In step 131, system 130 receives the order. System 130 may wait to receive necessary medical test results to fulfill the order.

In some embodiments, the intermediary system 120 and system 130 are each hosted in external computer systems by an interpretation provider and are external to the client 110 and EHR 111. In some embodiments, intermediary system 120 is optional and system 130 connects directly to client 110, EHR 111, and review system 112. System 130 may connect to plurality of different clients, EHR, and review systems and may receive data in different formats from different EHRs and convert the data into a canonical format for processing.

Medical lab providers may prepare and transmit medical test data to the EHR 111. The medical lab providers may generate medical test data in computer systems external to the client 110, intermediate system 120, and system 130, and may transmit the data from the external computer systems to EHR 111. Medical test data may comprise, for example, medical test results, lab results, vitals, data contributing to a diagnosis, and so on. The EHR 111 populates fields in the patient medical chart with the medical test data. The EHR 111 may transmit the medical test data over VPN 122 to intermediary system 120, which maps the medical test data to a canonical format. The intermediary system 120 transmits the medical test data over REST API 124 to system 130. In step 132, system 130 receives the medical test data. In an alternative embodiment, medical lab providers may transmit medical test data from their external computer systems directly to intermediate system 120 or system 130 instead of to EHR 111. In some embodiments, medical test data may be optionally stored and retrieved from database 140. In some embodiments, an extract, transform, load (ETL) 144 system may be used out of band to store and retrieve data from database 140.

System 130 evaluates whether sufficient medical test data has been received to fulfill the order. In step 133, after determining that sufficient medical test data was received, system 130 interprets the received medical test data using a rules engine. In some embodiments, the rules engine comprises one or more interpretation rules for generating an interpretation from a data set of medical test data. The interpretations may comprise text and an optional identifying code. In some embodiments, a plurality of pre-configured interpretations are stored in a comments file 142 that is provided by a pathologist 152. The rules engine, based on interpretation rules, selects an appropriate pre-configured interpretation from comments file 142 based on the medical test results. In some embodiments, the pre-configured interpretations may be identified by a code value that may be transmitted to the EHR along with the interpretation text.

In step 134, system 130 generates order results including the generated interpretation. System 130 transmits the order results over API 124 to intermediary system 120. The intermediary system 120 maps the order results into a format readable by review system 112. Intermediary system 120 may interface with a plurality of review systems that each read order results in different formats. In some embodiments, the review system 112 comprises a component of EHR 111, while in other embodiments it is an external computer system. The intermediary system 120 transmits the order results over VPN 122 to the review system 112. The review system 112 queues received order results and interpretations for review and approval by a pathologist 152. The interpretation is displayed in review system 112 to pathologist 152, who approves or declines the interpretation. When the interpretation is approved, the interpretation is released into the EHR 111 where it is stored and displayed as a part of the patient's medical chart in the EHR 111. The interpretation is integrated with the rest of the patient's medical information in the EHR 111 where it can be viewed and used by the clinician 150. If the interpretation is declined, then the interpretation and order is cancelled without being added to patient chart in EHR 111. In some embodiments, client 110 may employ pathologist 152 and provide and host the computer system of the review system 112.

Figure 2:
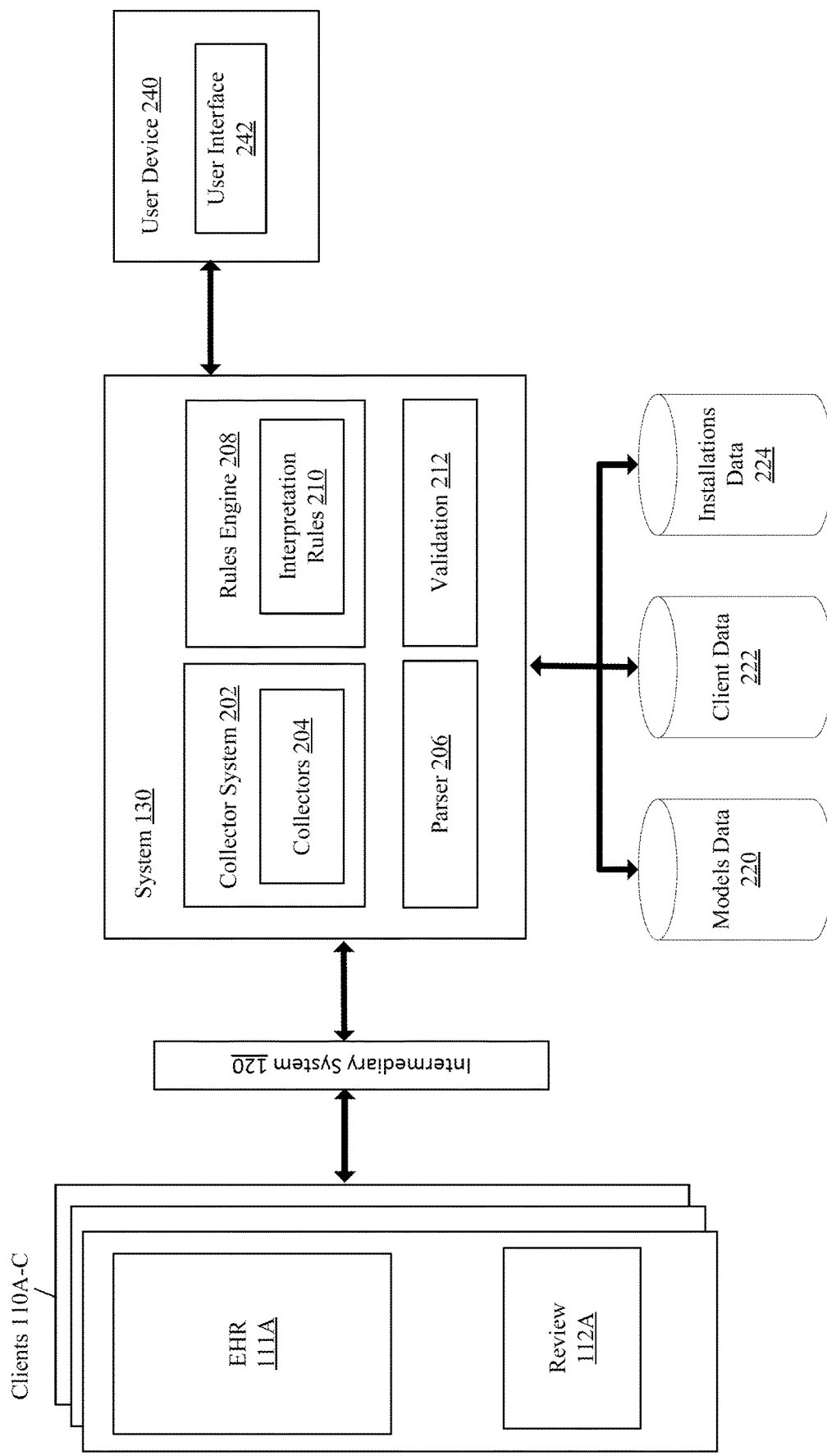
FIG. 2 illustrates an exemplary block diagram showing a system.

FIG. 2 illustrates an exemplary block diagram showing system 130. A plurality of clients 110A-C interface with intermediary system 120, which maps their data to a canonical format and interfaces with system 130. Client 110A includes EHR 111A and review system 112A and the other clients similarly have their own EHR and review systems that may differ from EHR 111A and review system 112A.

System 130 may include a collector system 202, collectors 204, parser 206, rules engine 208, interpretation rule 210, and validation system 212. Collector system 202 may comprise an asynchronous job based system for creating collectors 204 based on events from EHRs. Collectors 204 may comprise asynchronous processes and software for receiving and processing events from EHRs. Parser 206 may parse events, values, and data received from EHRs. Rules engine 208 may analyze one or more data values of medical tests to generate an interpretation. Interpretation rules 210 may comprise one or more rules in the rules engine 208 for analyzing data values to generate an interpretation. Validation system 212 may validate data from EHRs and pass on orders for processing or cancel orders as appropriate.

In some embodiments, optional data sets can include one or more of models data 220, client data 222, and installations data 224. Models data 220 may comprise one or more medical test processing models for processing data values from medical tests to generate an interpretation. Client data 222 may comprise information associated with clients interfacing with system 130 such as clients 110A-C. Installations data 224 may comprise information associated with the installation of models for particular clients 110A-C and may include configuration mappings for converting data and code values of clients 110A-C to data and code values usable by medical test processing models.

In some embodiments, optional user device 240 is a device allowing interfacing with the system 130 from one or a plurality of devices. User device 240 may include a display configured to present information to a user in the form of a user interface 242. User device 240 may send and receive signals and information to the system 130. User interface 242 displayed on user device 240 may include one or more admin displays for configuring, managing, and maintaining operation of system 130 and viewing and editing data in system 130. In some embodiments, user device 240 is optional and user interface 242 may be located in system 130 where users may use the user interface 242 on system 130.

Figure 3:
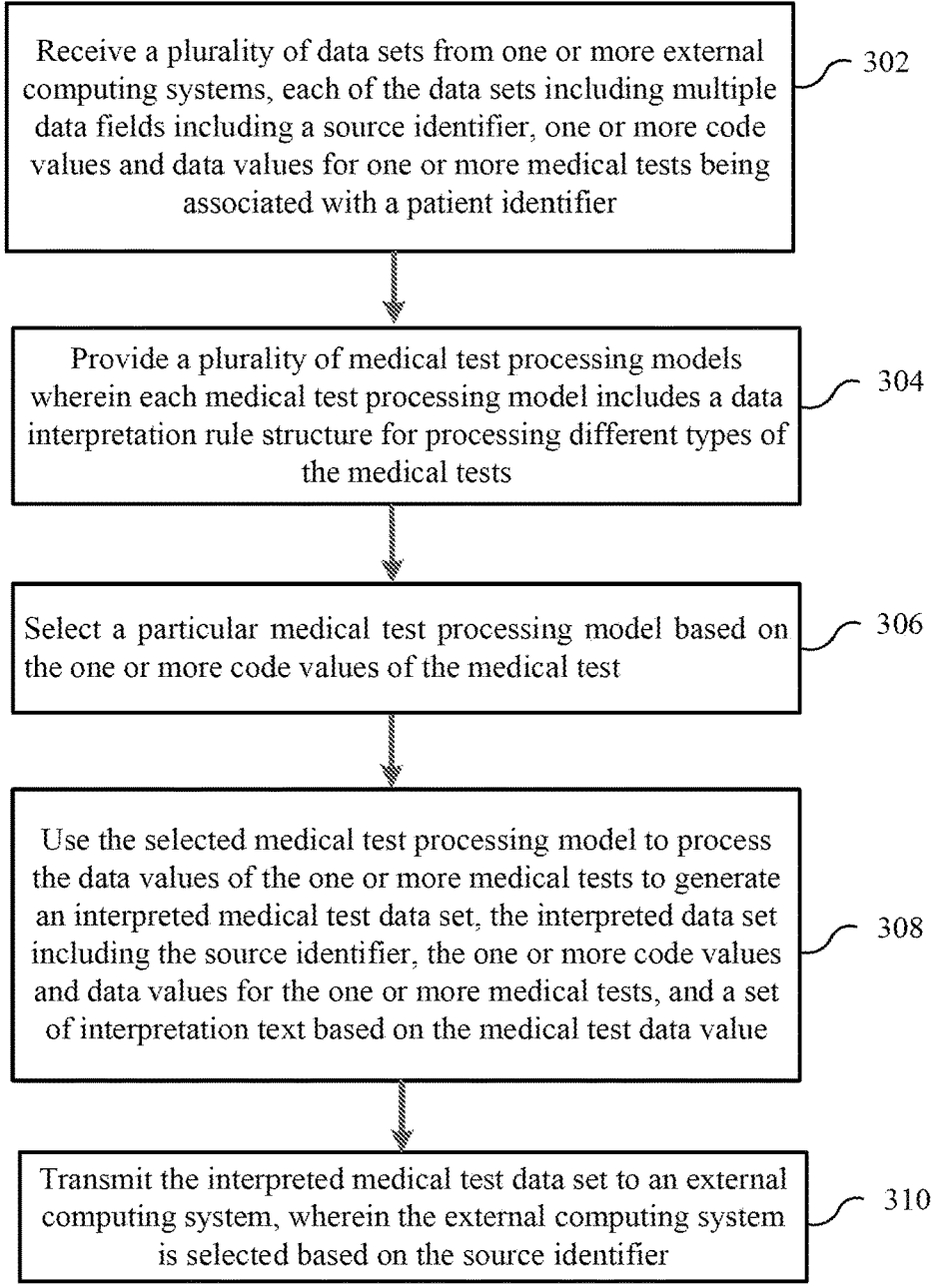
FIG. 3 is a flow chart illustrating an exemplary method for generating an interpreted medical test data set.

FIG. 3 is a flow chart illustrating an exemplary method 300 for generating an interpreted medical test data set. In step 302, system 130 receives a plurality of data sets from one or more external computing systems, each of the data sets including multiple data fields including a source identifier, one or more code values and data values for one or more medical tests being associated with a patient identifier. In some embodiments, the data sets may comprise one or more orders from clients for interpretation of the medical test data values. The data sets may be received from external computing systems at clients 110A-C hosting EHRs and may be received via intermediary system 120. The source identifier of the data set may comprise a text or code value identifying the client that is the source of the data set. The patient identifier of the data set may comprise a text or code value identifying a patient associated with the data set, such as a medical record number (MRN), hash value, or other identifier. Medical tests in the data set may include code values identifying the type of test (such as an Immunoglobulin G (IGG), Immunoglobulin M (IGM), basic metabolic panel (BMP), complete blood count (CBC), and so on) and data values identifying the data collected or results of the tests.

In step 304, system 130 provides a plurality of medical test processing models wherein each medical test processing model includes a data interpretation rule structure for processing different types of the medical tests. Each medical test processing models may correspond to a type of interpretation that the model generates. For example, a first medical test processing model may be for generating an interpretation of toxicology medical tests and a second medical test processing model may be for generating an interpretation of COVID-19 medical tests. In some embodiments, the medical test processing models may be stored in models data 220.

In step 306, the system 130 selects a particular medical test processing model based on the one or more code values of the medical test. In some embodiments, EHR 111 includes a code value in an order that identifies an interpretation type requested by the clinician 150. For example, a request for a toxicology interpretation may have code TOX and a request for a COVID-19 interpretation may have code COVID19. The code value identifying the interpretation type may comprise a code value of the medical tests and may be used by the system 130 for selecting a particular medical test processing model to generate the interpretation type requested by the clinician 150.

In step 308, the system 130 uses the selected medical test processing model to process the data values of the one or more medical tests to generate an interpreted medical test data set, the interpreted data set including the source identifier, the one or more code values and data values for the one or more medical tests, and a set of interpretation text based on the medical test data value. In some embodiments, the system 130 runs a computation using the selected medical test processing model to process the data values to generate interpretation text. The system 130 may package the interpretation text with the source identifier, one or more code values and data values for the one or more medical tests into an interpreted medical test data set.

In step 310, the system 130 transmits the interpreted medical test data set to an external computing system, wherein the external computing system is selected based on the source identifier. In some embodiments, the system 130 uses the source identifier to identify the associated client and transmits the interpreted medical test data set to the external computing system of the client, such as the review system 112 or EHR 111. The system 130 may interface with a plurality of external computing systems corresponding to different clients and, therefore, use of the source identifier allows returning the interpreted medical test data set to the appropriate source.

Figure 4:
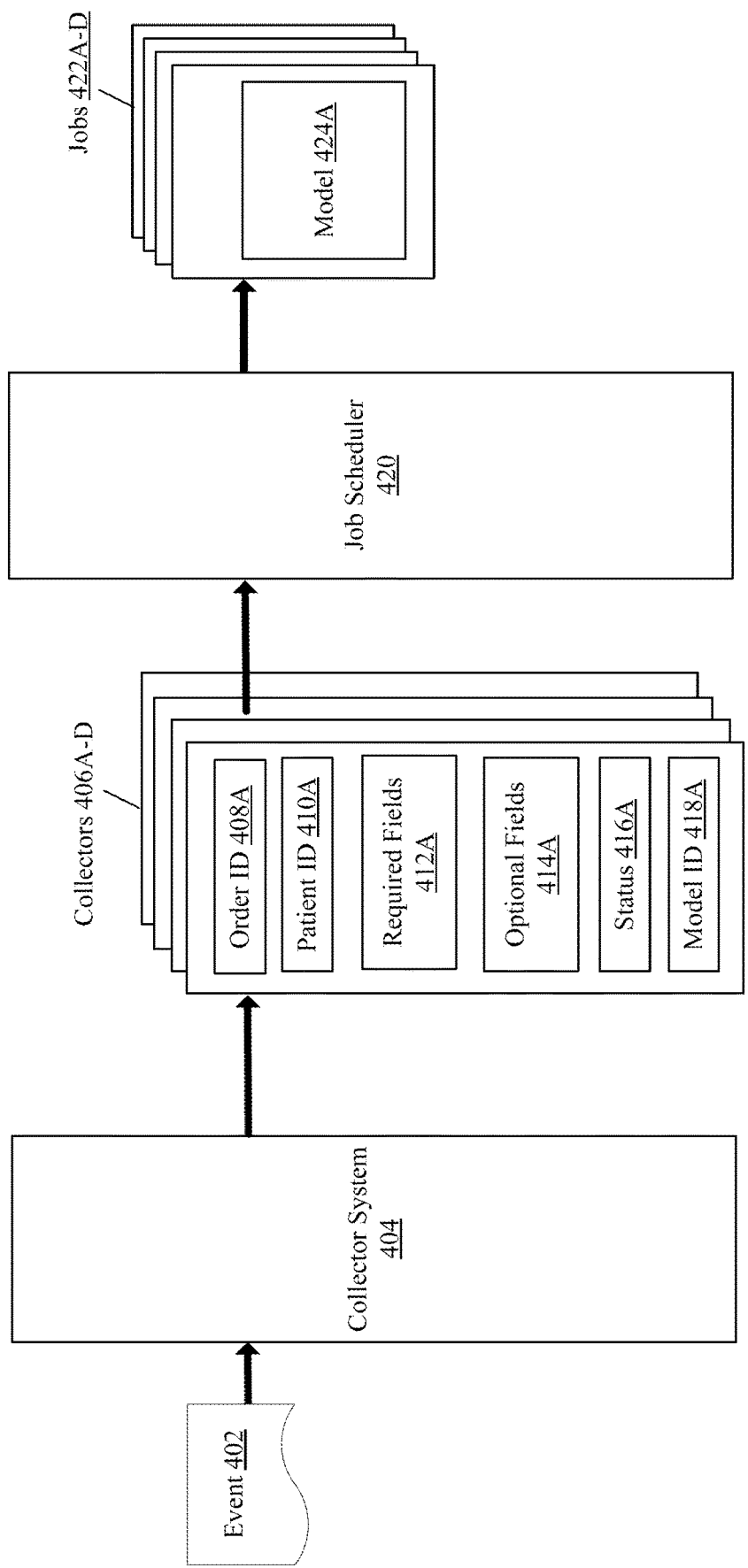
FIG. 4 illustrates an exemplary block diagram of an asynchronous job based collector system for handling events and scheduling jobs to run one or more medical test processing models to generate interpretation text.

FIG. 4 illustrates an exemplary block diagram of an asynchronous job based collector system for handling events and scheduling jobs to run one or more medical test processing models to generate interpretation text. Event 402 may be transmitted by EHR 111 and received by the system 130. Event 402 may comprise one of at least two different types of events, including at least (1) creation of an order for an interpretation type and (2) data values of a completed medical test. Event 402 may include an identifier of the type of event and associated values such as source identifier, patient identifier, one or more code values and data values for one or more medical tests, and so on. In some embodiments, event 402 may comprise the data set in step 302. In some embodiments, event 402 comprises data in a structured format such as JavaScript Object Notation (JSON) or extensible markup language (XML) that is used by or native to the EHR 111 or intermediary system 120. The parser 206 may parse the data in the event 402 to extract the data values from the structured data format.

Collector system 404, collectors 406A-D, job scheduler 420, and jobs 422A-D may reside in system 130. Collector system 404 may comprise an asynchronous job based system for creating collectors to asynchronously monitor events received from EHRs of clients 110A-C and handle them as necessary. Collectors 406A-D may reside in a collector pool and may each include data such as order ID 408A, patient ID 410A, required fields 412A, optional fields 414A, status 416A, and model ID 418A. Order ID 408A may identify an order associated with the collector. Patient ID 410A may identify a patient associated with the collector. Required fields 412A may identify medical test fields that the collector requires to schedule computation of the medical test processing model and for which the collector will await receipt. Optional fields 414A may identify medical test fields that are not required for the collector to schedule computation of the medical test processing model but which can increase accuracy of the interpretation. Status 416A may record the status of the collector, where the collector is in a status of Waiting while waiting for additional medical test data values and changes status to Ready when all necessary medical test data values are received to allow processing the medical test processing model. Model ID 418A may identify the medical test processing model that the collector will schedule when the status changes to Ready.

Job scheduler 420 receives requests from collectors 406A-D to schedule a job to process a medical test processing model to generate interpretation text. In response to receiving a request, job scheduler 420 creates a job and adds it to the job pool. Jobs 422A-D are jobs in the job pool. Each job processes a medical test processing model, such as model 424A, using the data values from required fields 412A and/or optional fields 414A to generate interpretation text. The medical test processing model generates interpretation text that system 130 includes in interpreted medical test data set and transmits to a review system of one of the plurality of clients based on the source identifier. After processing, the job may be removed from the job pool. The system 130 may transmit the interpretation text to the client 110A-C into the review system.

Figure 5:
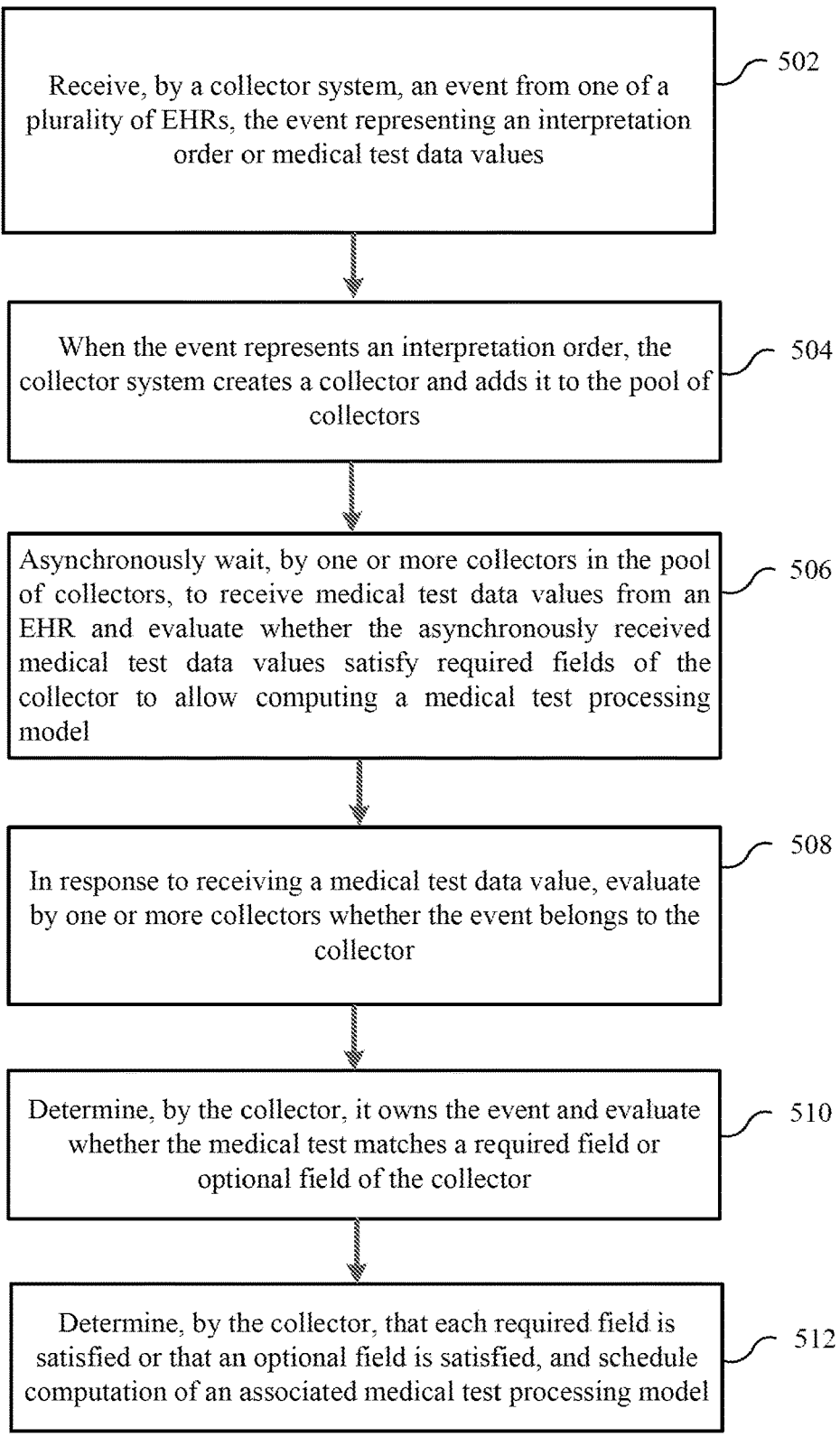
FIG. 5 is a flow chart illustrating an exemplary method for using an asynchronous job based system of collectors to wait for medical test data values and schedule computation of a medical test processing model.

FIG. 5 is a flow chart illustrating an exemplary method 500 for using an asynchronous job based system of collectors to wait for medical test data values and schedule computation of a medical test processing model.

In step 502, the collector system 404 receives an event from one of a plurality of EHRs, the event representing an interpretation order or medical test data values. The interpretation order may comprise an order from a clinician 150 to interpret medical test data values. The medical test data values may comprise data values from a completed medical test.

In step 504, when the event represents an interpretation order, the collector system 404 creates a collector and adds it to the pool of collectors. The interpretation order may include data such as: an order identifier, patient identifier, and an interpretation code value. The order identifier may represent a unique identifier of the order from the clinician 150 to allow tracking and matching and may be stored in the collector as order ID 408A. The patient identifier may uniquely identify the patient and may be stored in the collector as patient ID 410A. The interpretation code value may uniquely identify the type of interpretation requested by the clinician 150 (e.g., toxicology interpretation, COVID-19 interpretation, and so on). Based on the interpretation code value, the collector system 404 may identify a corresponding model identifier for the medical test processing model to generate the requested interpretation and store it as model ID 418A. The medical test processing model, as stored in models data 220, may include required fields for running the model and optional fields for running the model, which may be stored as required fields 412A and optional fields 414A, respectively.

In an embodiment, the interpretation order from the EHR does not include data values of medical tests that are necessary for performing the interpretation. In some embodiments, the interpretation order includes no data values of medical tests, rather the interpretation order includes only the order and the medical test data values are transmitted as separate events to system 130. The collector cannot proceed with running the medical test processing model without the medical test data values and so must wait for the medical test data values to be received.

In step 506, the collectors 406A-D asynchronously wait to receive medical test data values from an EHR and evaluate whether the asynchronously received medical test data values satisfy required fields of the collector to allow computing a medical test processing model. The collectors 406A-D stay in a Waiting status and their stored values 408A, 410A, 412A, 414A, 416A, 418A allow them to maintain saved state while waiting for medical test data values to arrive from one or more of the EHRs.

In step 508, in response to receiving a medical test data value, one or more collectors evaluate whether the event belongs to the collector. In an embodiment, the plurality of EHRs transmit an event to system 130 each time new medical test data values are received at the EHR to update system 130 regarding the new medical test data. The event includes an order identifier, patient identifier, and one or more code values and data values for one or more medical tests. In an embodiment, collector system 404 passes each event to each of collectors 406A-D, and collectors 406A-D compare the order identifier and patient identifier of the event with their own order ID 408A and patient ID 410A. When a collector determines a match on both the order identifier and patient identifier, the event is for the order of the collector, and the collector performs further processing. When a match is not found, the event is not for the order of the collector, and the collector may ignore the event.

In step 510, a collector determines it owns the event and evaluates whether the medical test matches a required field or optional field of the collector. In an embodiment, a collector determines it owns the event when a match is found on both the order identifier and patient identifier. In some embodiments, the collector compares a code value of the medical test in the event to a first set of code values identifying required fields and a second set of code values identifying optional fields. When a match with the first set or second set of code values is found, the collector determines that the medical test is a required field or optional field, respectively. In response to a match, the collector updates its stored values of required fields 412A and optional fields 414A to store data values of the medical test of the event in the collector and reflect that data values for a required field or optional field have been received.

In step 512, the collector determines that each required field is satisfied or that an optional field is satisfied, and schedules computation of an associated medical test processing model. When new data values from a medical test are stored in the collector, the collector evaluates whether all of the required fields are completed or an optional field is completed. When all required fields are completed, then data values for all necessary medical tests for processing the medical test processing model have been received. The collector changes its status to Ready and transmits a request to job scheduler 420 to schedule a job to process the medical test processing model for model ID 418A. The collector remains in the collector pool to continue to wait for any further medical test data values events matching an optional field 414A that may necessitate scheduling a new job to process the medical test processing model again to generate an updated interpretation.

In some embodiments, events may be received from EHRs for medical tests that are optional fields that increase the accuracy of interpretations but are not required. When data values for the optional medical tests are received, the system 130 may re-process the medical test processing model by adding the data values of the optional medical test in addition to the data values that were previously received for other medical tests to generate new interpretation text.

In an embodiment, when a collector determines that a received event identifies a medical test matching an optional field 414A, the collector evaluates whether all the required fields 412A are completed. When collector determines that all the required fields 412A are completed and data values are received for an optional field 414A, then the collector transmits a request to job scheduler 420 to schedule a job to process the medical test processing model for model ID 418A using the data values of the new optional medical test in addition to previously stored data values of required and optional fields. The medical test processing model generates a new interpretation text that is transmitted to review system 112. When approved by the pathologist 152, the new interpretation text may be added to the EHR 111 and may replace a previously generated interpretation text that may have been added to the EHR 111 for the patient. The process may be repeated for additional optional medical tests that are received and match optional fields 414A, so that the medical test processing model may be repeatedly processed to generate updated interpretation text that replaces prior interpretation text.

Accordingly, system 130 provides for iteratively updating interpretation text based on newly received optional medical test data values, when required medical test data values have been previously received. The iterative updating may be performed repeatedly for a plurality of optional medical test data values that are received by the system 130 at different times. The system 130 may aggregate the medical test data values received up to the current time and input the medical test data values into the medical test processing model to generate a most-up-to-date interpretation text. Each of the iterative updates replaces previously generated interpretation text in the EHR with a more accurate interpretation text that is updated based on the newly received optional medical test data values.

Figure 6A:
FIG. 6A illustrates an exemplary user interface for viewing medical test processing model definitions.

FIG. 6A illustrates an exemplary user interface 600 for viewing medical test processing model definitions. In the exemplary user interfaces herein, medical test processing models may be referred to as products. For example, a "product definition" may refer to definition of a medical test processing model. A list of medical test processing models is displayed in list 602. For each medical test processing model, user interface 600 displays an identifier and a type. The type may comprise a code value identifying the type of interpretation performed by the medical test processing model, such as COVID_INTERP for COVID-19 interpretation. A button or user interface element may be displayed for allowing the user to create a new medical test processing model. Menu bar 601 may enable navigation of the admin system to view and manage other aspects of the configuration and data of system 130. Menu bar 601 may include user interface elements for viewing and searching medical test processing models ("Product Definitions"), viewing and searching configurations, viewing and searching order results, configuring intermediary system 120, viewing and searching clients, viewing and searching collectors, viewing the job queue, configuring feature switches, and sending email and other notifications. In response to user selection of one of the menu bar 601 user interface elements, a corresponding user interface screen is displayed.

FIG. 6B illustrates an exemplary user interface 610 for viewing a medical test processing model definition. In the exemplary user interface 610, the "Product Definition Info" refers to a medical test processing model definition. In an embodiment, the user interface 610 is displayed in response to receiving a user selection of a medical test processing model in user interface 600 to display more detail.

Basic model definition info 611 is displayed including the identifier, type, and minimum and maximum patient age for the medical test processing model. User interface 610 displays a list of input fields 612 for the medical test processing model. Each of the input fields 612 corresponds to a medical test that may be a required field or optional field for running the medical test processing model.

Each of the input fields may include a code, name, value type, max value, min value, units, and lab results window. The code may comprise an identifier 842A-C for the medical test. The name may comprise a human-readable name for the medical test. The value type may comprise the type of data values that are valid for the medical test. The max value and min value may comprise a range definition of valid values for the medical test. A units field may indicate the units of for the medical test. In some embodiments, each input field may be flagged as required or optional. The aforementioned fields may optionally be editable by a user. A button or user interface element is displayed for allowing a user to add a new input field to the medical test processing model and enter values for each of the aforementioned fields.

User interface 610 displays a list of computed results 613. The computed results allow configuring the output generated by the medical test processing model. In some embodiments, the user may configure whether the medical test processing model outputs an interpretation text or a number. For each computed result in list 613, a code value is displayed corresponding to the computed result. The InterpOutput code value may comprise an interpretation text output.

In some embodiments, user interface 610 may include one or more fields for configuring interpretation rules for the medical test processing model. User interface 610 may enable adding new interpretation rules to the medical test processing model and editing existing interpretation rules for the medical test processing model.

FIG. 6C illustrates an exemplary user interface 620 for viewing clients. A list of clients is displayed in list 621. For each client, user interface 620 displays an identifier, name, patient lookup value, allows generated test data flag, collector TTL days, and inputs TTL days. The name may comprise the source identifier for the client. The patient lookup value may comprise a code value identifying the field containing the patient ID in an event received from the client EHR. The fields may optionally be editable by a user. A button or user interface element is displayed for allowing the user to create a new client.

FIG. 6D illustrates an exemplary user interface 630 for viewing client information. In an embodiment, the user interface 630 is displayed in response to receiving a user selection of a client in user interface 620 to display more detail.

Basic client info 631 is displayed including the identifier, name, patient lookup value, and allows generated test data flag. User interface 630 displays a list of product installations 632 for the client. Each of the product installations corresponds to a medical test processing model that has been enabled (e.g., "installed") for the client.

Each of the product installations in list 632 includes an identifier, status, trigger order code, product definition, data provider, prov event sources, prov results destination, and model version. The identifier may comprise a unique identifier for the product installation. The status may comprise a status flag of enabled or disabled for the client. The trigger order code may comprise a code value identifying the product installation in an order from the client EHR. The product definition may comprise a code value identifying the medical test processing model that is associated with the installation. The data provider may comprise an identifier of the intermediary system 120 for receiving data values. The aforementioned fields may optionally be editable by a user. A button or user interface element is displayed for allowing a user to add a new installation to the client and enter values for each of the aforementioned fields.

User interface 630 displays a list of data provider order results 633. The data provider may correspond to intermediary system 120 providing data values from EHR. The list 633 may display a list of events from the EHR comprising data values from medical tests. Each event in the list comprises an identifier, a client identifier, data provider identifier (e.g., intermediary system 120), data provider event identifier (e.g., intermediary system event identifier), data provider order code (e.g., code value 824 identifying the medical test), and creation time stamp. Each event is processed by collectors to identify a matching collector that owns the event. The collector evaluates the code value identifying the medical test to determine whether it matches a required or optional field of the collector.

Figure 6E:
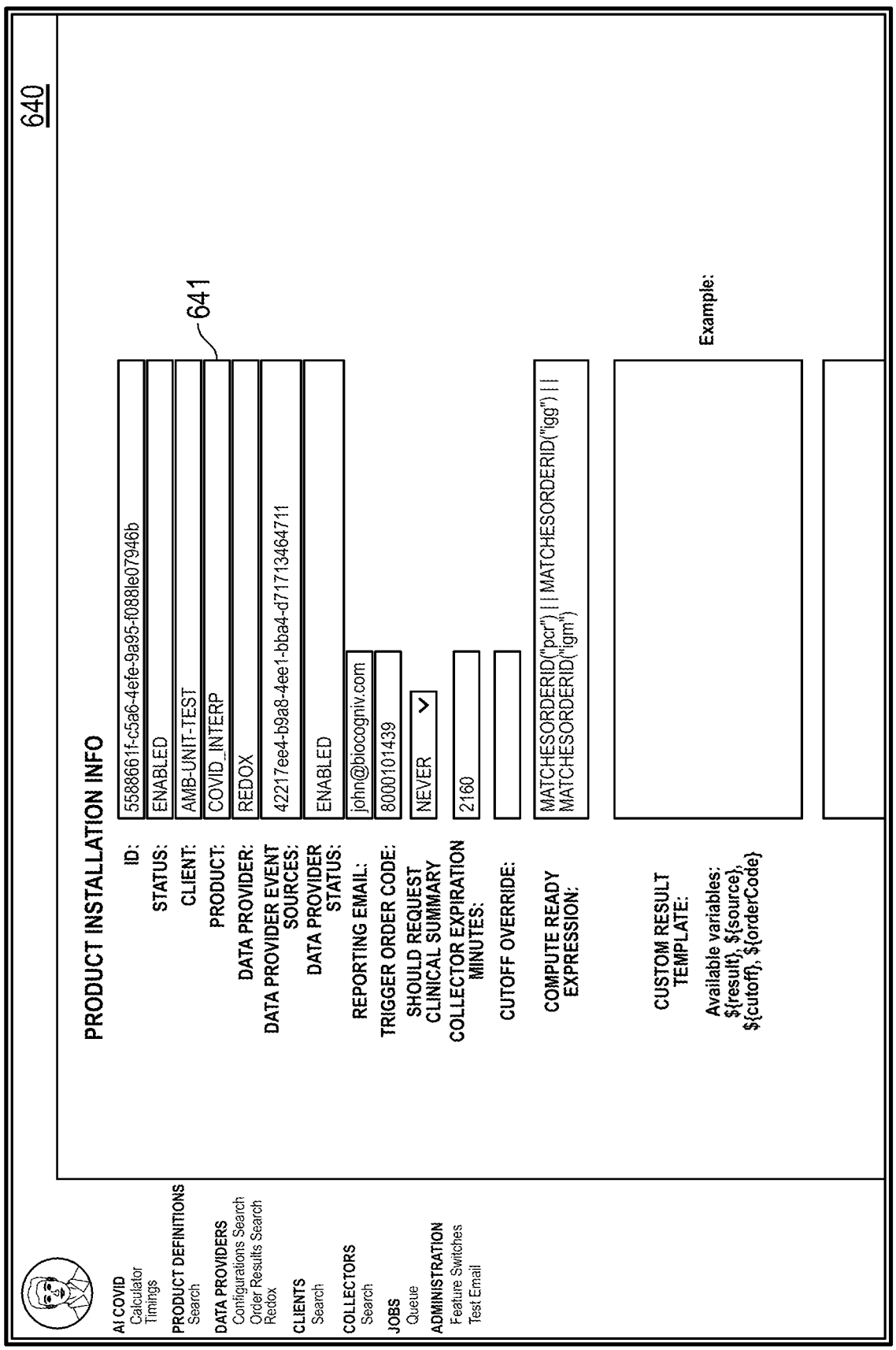
FIG. 6E illustrates an exemplary user interface for viewing product installation information.

FIG. 6E illustrates an exemplary user interface 640 for viewing product installation information. In an embodiment, the user interface 640 is displayed in response to receiving a user selection of a product installation in user interface 630 to display more detail.

Basic product installation info 641 is displayed including the identifier, status, client identifier, product identifier, data provider, data provider event sources, data provider status, reporting email, and trigger order code. Additional fields are displayed for reporting email, trigger order code, should request clinical summary flag, collector expiration minutes, and cutoff override. The aforementioned fields may optionally be editable by a user.

FIG. 6F illustrates an exemplary user interface 645 that is a continuation of the user interface 640. User interface 645 displays a list of field mappings 646. The field mappings 646 map between medical test code values 824 in events from the EHR, which are displayed for example in the "Data Provider Order Code" field of order results list 633, and medical test code values 842A-C in a medical test processing model, such as the code values of input field list 612. Different EHR systems have different code values for the same medical test. For example, a PCR test for COVID-19 might have a code value of COVID19 in one EHR and COVID19PCR in another EHR. These code values in different EHRs are received by the system 130 in EHR events. The field mappings 646 map from these different EHR event code values to the same code value identifying the underlying medical test that is used in the medical test processing model.

Each field mapping 646 includes an identifier, product field code, source type, installation order code, installation result code, installation units, required to compute, expression, and normalization expression. The identifier may comprise a unique identifier for the field mapping. The product field code may identify the code value of the medical test 842A-C in the medical test processing model, which is in other words the target of the field mapping. The source type may comprise an identifier of the type of medical test, such as a lab result. The installation order code may comprise the code value 824 received from the EHR, which may be different between EHRs and is in other words the source of the field mapping. The required to compute field may comprise a flag identifying whether a data value for the medical test is required to compute the medical test processing model. The aforementioned fields may optionally be editable by a user. For example, the product field code and installation order code may both be user editable to allow configuration of field mappings. A button or user interface element is displayed for allowing a user to add a new field mapping to the product installation and enter values for each of the aforementioned fields.

User interface 645 displays a list of result mappings 647. The result mappings 647 map between a code value of an output of a medical test processing model and a code value identifying the output in the EHR. Each result mapping 647 includes an identifier, product code (e.g., the code value of the medical test processing model 613), and provider code. The provider code may be a code value identifying the type of interpretation output value in the EHR (e.g., toxicology interpretation, COVID-19 interpretation, and so on).

Figure 6G:
FIG. 6G illustrates an exemplary user interface for viewing collectors.

FIG. 6G illustrates an exemplary user interface 650 for viewing collectors. A list of collectors is displayed in list 651. For each collector, user interface 650 displays an identifier, an ordered at timestamp, a created at timestamp, product type, client identifier, patient identifier, status, cancel reason, expire after timestamp, clinical summary status, and result data ready counter. The ordered at timestamp and created at timestamp may identify the time that the collector was ordered and created, respectively. The product type may identify the medical test processing model associated with the collector. The client identifier may comprise a source identifier of the client. The patient identifier may comprise a unique identifier of the patient associated with the collector.

The status may comprise an identifier of the status of the collector. A status of Closed may indicate that the collector is closed and is not waiting for any further medical test data value events and will not accept any medical test data value events if received. A status of Open may indicate that the collector is waiting to receive medical test data value events and the required medical test data values have not yet been received to enable processing the medical test processing model. A status of Computed may indicate that the collect has received the required medical test data values and computed at least one generated output from the medical test processing model, and the collector remains waiting for optional medical test data values that may be received for generating updated output from the medical test processing model. A status of Error may indicate that an error occurred.

The cancellation reason may comprise an identifier of a reason for cancellation of a collector. The expire after timestamp may identify an expiration time for the collector. In some embodiments, collectors may have a set time to remain live before they expire. Collectors remain waiting for medical test data value events while they are live, even when they may have already computed the medical test processing model one or more times because optional medical test data values may be received. In some embodiments, the expiration time is provided by the client 110 or EHR 111 based on how long the client is willing to wait for an interpretation. For example, expiration may be a matter of minutes, hours, days, and so on from the collector's ordered at time. When the expiration time is reached, the collector enters the Closed status and does not receive further events.

Clinical summary status may indicate whether an interpretation output has been generated. Result data ready may comprise a count of the number of medical test data values received out of the total number of medical tests possible for the collector. For example, a value of ⅔ may indicate that 2 medical tests have received data values out of 3 possible medical tests of the collector.

FIG. 6H illustrates an exemplary user interface 660 for viewing collector information. In an embodiment, the user interface 660 is displayed in response to receiving a user selection of a collector in user interface 650 to display more detail.

Basic collector info 661 is displayed including the identifier, status, ordered at timestamp, cancellation reason, failure metadata, client identifier, patient identifier, visit identifier, product installation identifier, order identifier, application order identifier, expire after timestamp, and data provider order identifier. User interface 660 displays a list of mapped result data 662 for the collector. Each of the mapped result data elements 662 correspond to a medical test of the collector. For each medical test, the user interface 660 displays a product code, value, source series, resulted at, value status, failure reason, event identifier, and last event identifier. The product code may comprise a code value 842A-C identifying the medical test and may match, for example, the code values of medical tests in the medical test processing model definition in list 612. The value may comprise the data value 822 received from the EHR for the medical test. For example, the value may comprise a Boolean value (e.g., positive or negative), a numerical value, or other values. The value status may comprise a status of the data values for the medical test. For example, a status of waiting may indicate that the collector is waiting for data values for the medical test, while a status of valid may indicate that the data values for the medical test are valid. The event identifier may identify the event from the EHR that provided the data values for the medical test. Table 663 displays further information regarding the medical tests of the collector. User interface element 665 may allow showing or hiding additional information.

Computed data 664 may comprise one or more outputs that have been generated as a result of the collector scheduling a job to run a medical test processing model. Each computed data element 664 may include a code value, event, value, and value type. The code value may identify the type of output of the medical test processing model that was output, such as one of the output types from list 613. The value may comprise an identifier of the output that was generated by the medical test processing model. In the illustrated example, the identifier indicates that interpretation number 75 from the comments file was selected by the medical test processing model. The value type may comprise an identifier of the value type of the output.

User interfaces 600, 610, 620, 630, 640, 645, 650, 660 and other user interfaces herein may comprise portions of an admin system on system 130.

FIG. 7 is a flow chart illustrating an exemplary method 700 for a rules engine generating an output interpretation text. In step 702, system 130 provides a rules engine comprising multiple interpretation rules used to analyze the data values of the one or more values of a medical test, the interpretation rule including lookup data values. In some embodiments, each medical test processing model includes a data interpretation rule structure that comprises multiple interpretation rules. The system 130 may select a medical test processing model based on one or more code values of a medical test or order matching the code value of the medical test processing model as described in method 300. In some embodiments, each interpretation rule includes lookup data values that correspond to data value criterion that one or more data values must satisfy for the interpretation rule to apply. The lookup data values may correspond to data values of one or more medical tests. For example, an interpretation rule may have a lookup data value of positive for medical test A, which corresponds to a data value criterion that the medical test data value of medical test A must be positive. The interpretation rule may have a lookup data value of a numerical range of 214-470 for medical test B, which corresponds to a data value criterion that the medical test data value of medical test B must be in the range of 214-470. The interpretation rule may have a lookup data value of a ratio of more than 3.0 for medical test C, which corresponds to a data value criterion that the data values of two specified medical tests of medical test C must be have a ratio of more than 3.0.

In step 704, the system 130 selects an interpretation rule based on the data values of the medical test and the lookup data values. In some embodiments, the system 130 selects the interpretation rule from the set of interpretation rules in the data interpretation rule structure of the medical test processing model. The data interpretation rule structure of the medical test processing model may comprise a set of candidate interpretation rules. The rules engine 208 may evaluate one or more of the candidate interpretation rules to find a match. The rules engine 208 may compare the data values of one or more medical tests that have been received to the lookup data values of one or more candidate interpretation rules. The rules engine 208 may evaluate the data criterion of each lookup data value of the interpretation rule to determine whether it is satisfied by the data values of the medical tests. When the rules engine 208 determines that one of the candidate interpretation rules has all the data criterion of its lookup data values matched by the data values of the one or more medical tests, then that interpretation rule may be selected. When there is a mismatch between one of the data criterion of the lookup data values of the candidate interpretation rule and a data value of one or more medical tests, then that interpretation rule is not matched and the rules engine 208 continues to evaluate other candidate interpretation rules.

In step 706, the system 130 generates an output of the interpretation text where the interpretation rule includes lookup data values of the medical test corresponding to data value criterion of the interpretation rule. The interpretation rule may include one or more data value criterion for generating an output of interpretation text. The lookup data values of the interpretation rule may encode the data value criterion. When the data values of the medical test match the lookup data values of the interpretation rule, then interpretation text may be generated. In some embodiments, each interpretation rule is associated with a pre-configured interpretation text output. When the data value criterion of the interpretation rule is met, then the pre-configured interpretation text output is output as the generated interpretation text.

In some embodiments, the interpretation text output comprises a template with one or more dynamic fields. Each interpretation rule may be associated with a template that is output when the data criterion of the interpretation rule are met. The template may comprise a text template of an interpretation. The template also includes one or more dynamic fields in one or more locations of the text template. The dynamic fields operate like fill-in-the-blanks where the dynamic fields may be filled with values by the rules engine 208. In some embodiments, the rules engine 208 may fill dynamic fields with data values of a medical test, or other data values, such as numbers, booleans, ratios, and so on. For example, the template may include the text "The Fibrinogen count was {field_A}" where rules engine 208 fills in field_A with the data value of the Fibrinogen medical test. In some embodiments, the rules engine 208 may include a table of injectable text entries each having associated data criterion. The rules engine 208 selects a text entry based on one or more data values of a medical test satisfying the corresponding data criterion. For example, the rules engine 208 may evaluate that the data value of the Fibrinogen medical test is less than 214 and, when that data criterion is met, select a text entry of "The Fibrinogen count is low." Meanwhile, when the rules engine 208 evaluates that data value of the Fibrinogen medical test is more than 470, then it may select a text entry of "The Fibrinogen count is high." The selected text entry may be injected into a dynamic field of the template.

Figure 8A:
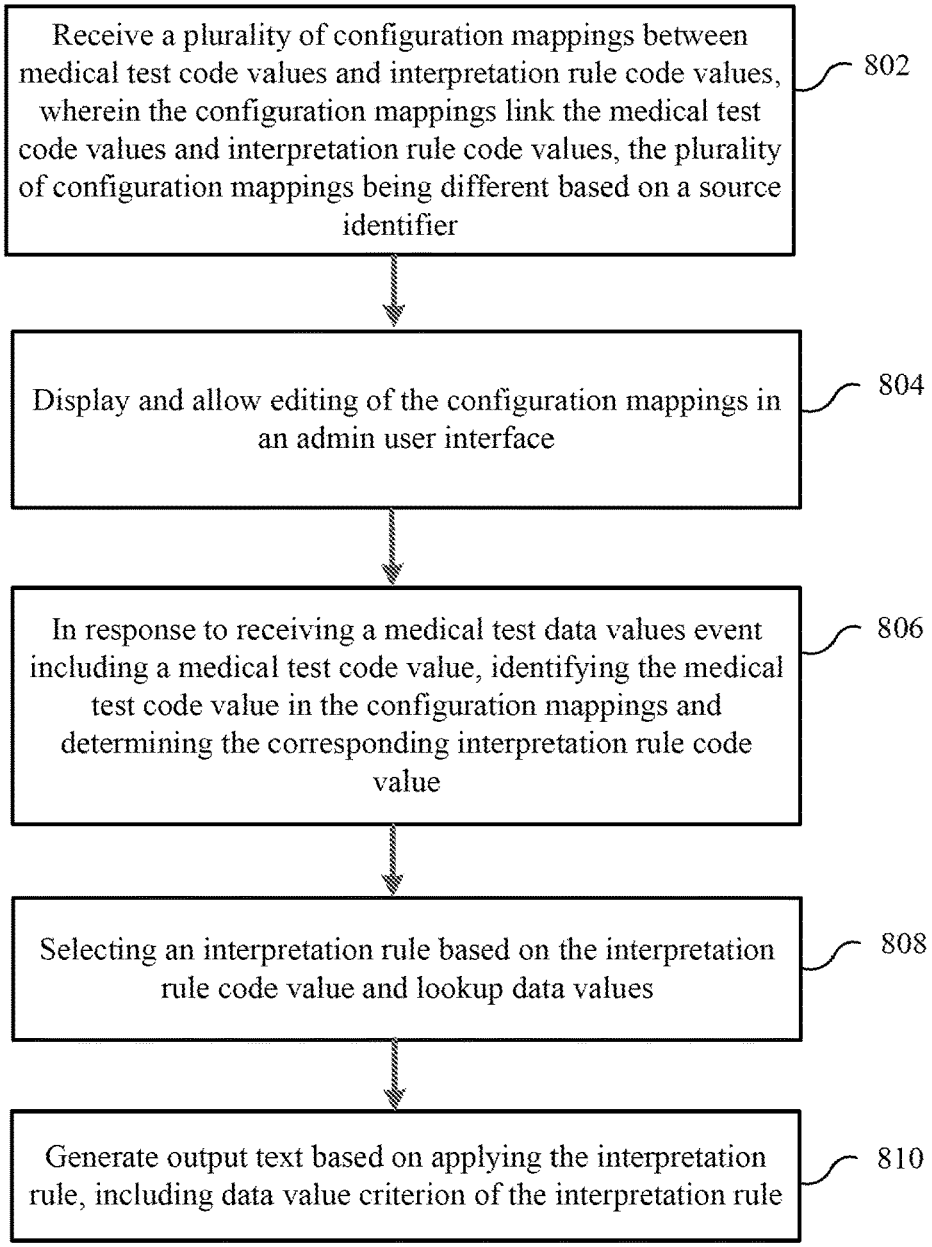
FIG. 8A is a flow chart illustrating an exemplary method for generating an output interpretation text based on a configuration mapping.

FIG. 8A is a flow chart illustrating an exemplary method 800 for generating an output interpretation text based on a configuration mapping. In step 802, the system 130 receives a plurality of configuration mappings 830 between medical test code values 824 and interpretation rule code values 842A-C, 844A-C, wherein the configuration mappings link the medical test code values 824 and interpretation rule code values 842A-C, 844A-C, the plurality of configuration mappings 830 being different based on a source identifier 832. In some embodiments, the configuration mapping 830 may be received from a user in the user interface 645 in field mapping list 646. The configuration mapping 830 may map a medical test code value 824 received in an event 402 from an EHR to a corresponding interpretation rule code value 842A-C, 844A-C, which identifies a medical test in a medical test processing model 424A. Configuration mappings 830 may differ between clients and EHRs. Configurations may be set by the user in user interface 645 for a product installation for a specific client. Each client may have a separate product installation having a different field mapping list 646 where different medical test code values are mapped to the interpretation rule code values.

In some embodiment, there may be a plurality of different medical test code values 824 that map to the same interpretation rule code value 842A-C, 844A-C. An EHR may have several different code values that may map to the same interpretation rule code value. For example, the medical test code values of COVID19 and COVID19R may both map to an interpretation rule code value PCR as illustrated in user interface 645.

In step 804, the system 130 displays and allows editing of the configuration mappings in an admin user interface. The admin user interface may comprise, for example, user interface 645.

In step 806, in response to receiving a medical test data values event 402 including a medical test code value 824, identifying the medical test code value in the configuration mappings 830 and determining the corresponding interpretation rule code value 842A-C, 844A-C. In some embodiments, the system 130 may receive an event 402 from the EHR including medical test data values 822. The event may include a medical test code value 824 identifying the medical test. The system 130 may use the configuration mappings 830 to map the medical test code value to an interpretation rule code value 842A-C, 844A-C.

In step 808, the system 130 selects an interpretation rule 842, 844 based on the interpretation rule code value 842A-C, 844A-C and lookup data values 842D-F, 844D-F. The system 130 may identify a candidate set of interpretation rules 842, 844 having a code value matching the code value 842A-C, 844A-C mapped in step 806. The system 130 may evaluate the interpretation rules based on the lookup data values 842D-F, 844D-F of the interpretation rules 842, 844 to find an interpretation rule matching the data values 822 of one or more medical tests.

In step 810, the system 130 generates output text based on applying the interpretation rule, including data value criterion of the interpretation rule.

Figure 8B:
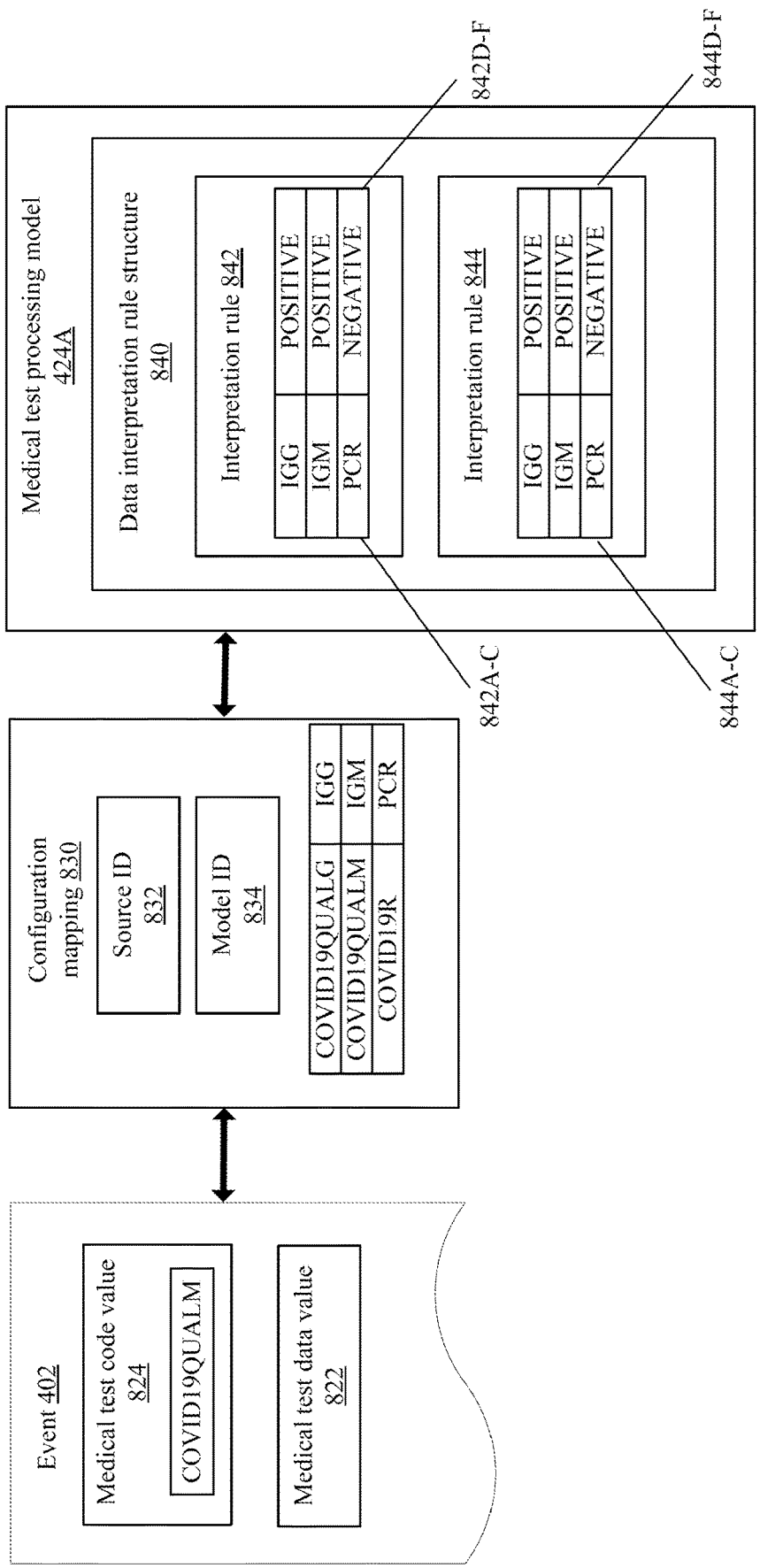
FIG. 8B illustrates an exemplary block diagram of a system for configuration mapping.

FIG. 8B illustrates an exemplary block diagram of a system for configuration mapping. Event 402 may be received from an EHR and may comprise a medical test code value 824 and medical test data value 822 associated with the medical test. In this example, the medical test code value comprises COVID19QUALM. The event 402 is mapped by configuration mapping 830. The configuration mapping 830 may comprise a source identifier 832 and model identifier 834. The system 130 may use the source identifier 832 and model identifier 834 to select the appropriate configuration mapping to use for event 402. Event 402 may be identified by a source identifier and order identifier. The system 130 may match the event 402 source identifier to the source identifier 832. The system 130 may map the event 402 order identifier to a collector 406A comprising a model identifier 418A, which is matched to the model identifier 834. When the source identifier and model identifier are matched, the configuration mapping 830 may be selected.

The configuration mapping 830 may include a table of mappings from medical test code values to interpretation rule code values. For example, the configuration mapping 830 maps COVID19QUALG to IGG, COVID19QUALM to IGM, and COVID19R to PCR. The mapped values may be used to associate the medical test data value 822 to the corresponding lookup data of an interpretation rule 842A-C, 844A-C.

Medical test processing model 424A may comprise a data interpretation rule structure 840, which may comprise a plurality of interpretation rules 842, 844. Each interpretation rule may comprise one or more code values 842A-C, 844A-C that each correspond to a lookup value 842D-F, 844D-F for a data value criterion. The code values 842A-C, 844A-C are mapped to the medical test code value 824 of event 402 via configuration mapping 830 to enable the lookup data values 842D-F, 844D-F to be compared to the corresponding medical test data value 822, when the interpretation rule code value 842A-C, 844A-C matches the medical test code value 824 of the event 402. The rules engine 208 may then identify a matching interpretation rule and generate output text using the method 800 or other methods described.

Figures 9A, 9B:
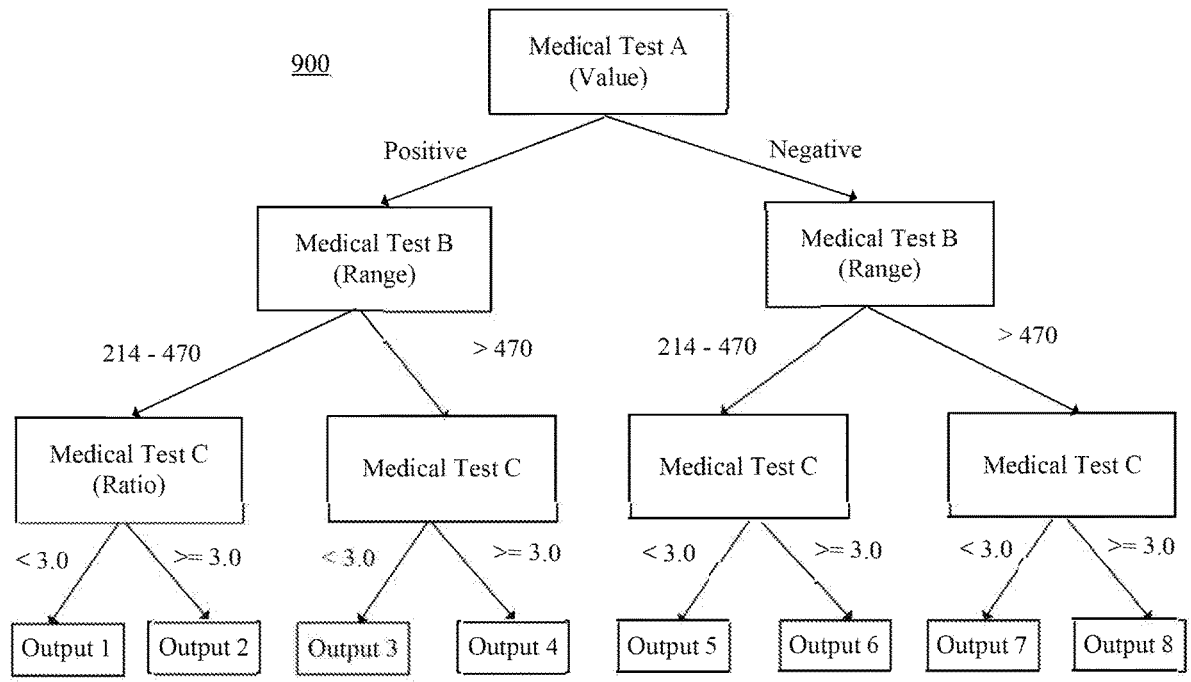
FIG. 9A illustrates an exemplary decision tree representation of a plurality of interpretation rules.
FIG. 9B illustrates an exemplary logic table of a plurality of interpretation rules.

FIG. 9A illustrates an exemplary decision tree representation 900 of a plurality of interpretation rules. In some embodiments, each interpretation rule may be multivariate because its output depends on a plurality of data criterion. In some embodiments, interpretation rules may be represented implicitly or explicitly as a decision tree 900. Evaluation by rules engine 208 begins at the root of the decision tree 900 and proceeds down to a leaf, each leaf corresponding to an output or to an error if no output is valid. Each node corresponds to a medical test, and the rules engine 208 branches based on the data value of the medical test that has been received. For example, when the data value of Medical Test A is positive, the data value of Medical Test B is in the range 214-470, and the data value of Medical Test C is a ratio of 3.0, then the output is output 1. Each path through the decision tree from the root to a leaf corresponds to an interpretation rule. When the data values of the medical tests match the required data lookup values of the interpretation rule at each branch, then the interpretation rule is selected and the output is generated.

Interpretation rules may include three different types of data criterion: value, range, and ratio. In a value criterion, the medical test data value is compared to a required value of the data criterion, and when it matches then the value criterion is satisfied. For example, the interpretation rule uses a value criterion for Medical Test A, where depending on the interpretation rule the data value of Medical Test A must be positive or negative. In a range criterion, the medical test data value is compared to a required range of the data criterion, and when the medical test data value falls in the range then the range criterion is satisfied. For example, the interpretation rule uses a range criterion for Medical Test B, where depending on the interpretation rule, the value of Medical Test B must fall between 214-470 or be greater than 470. In a ratio criterion, a ratio is generated between one or more medical test data values and is compared to a required ratio value of the data criterion, and when the generated ratio matches the required ratio value then the ratio criterion is satisfied. For example, the interpretation rule uses a ratio criterion for Medical Test C, where depending on the interpretation rule, the ratio of Medical Test C must be less than 3.0 or greater than or equal to 3.0.

FIG. 9B illustrates an exemplary logic table 910 of a plurality of interpretation rules. In some embodiments, interpretation rules may be represented implicitly or explicitly as a logic table 910. Rules engine 208 selects an interpretation rule by looking up in the logic table 910 the interpretation rule that matches the data values of one or more medical tests. Logic table 910 includes, for example, interpretation rule 1, interpretation 2, and interpretation rule 3. Each interpretation rule includes a data criterion for each of Medical Test A, Medical Test B, and Medical Test C, which are listed in the row. When the rules engine 208 selects an interpretation rule where each of the data criterion are satisfied by the data values of one or more medical tests, then the rules engine 208 may output the corresponding output shown in the row.

Figure 10:
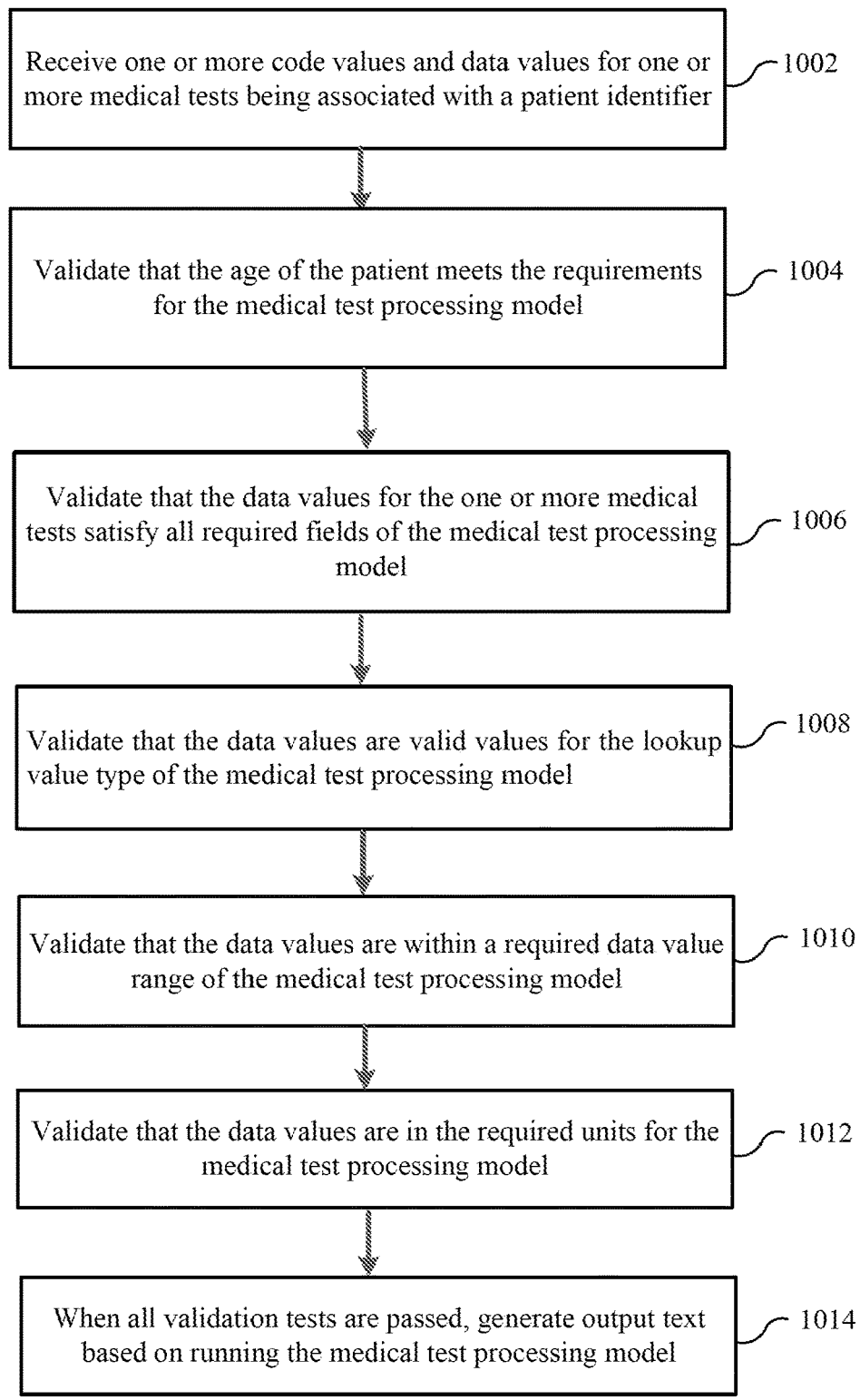
FIG. 10 is a flow chart illustrating an exemplary method for validating data.

FIG. 10 is a flow chart illustrating an exemplary method 1000 for validating data. In step 1002, the system 130 receives one or more code values and data values for one or more medical tests being associated with a patient identifier. For example, the system 1002 may receive code values and data values for one or more medical tests in an event 402 from an EHR, and the system 1002 may validate the code values and data values before processing the values.

In step 1004, the system 130 validates that the age of the patient meets the requirements for the medical test processing model. An order or event from an EHR may include patient biographical information such as age. In some embodiments, one or more medical test processing models have an age threshold, where the medical test processing model is only valid for patients within a certain age range or above or below a certain age. If the age requirement of the medical test processing model is not met, then the system 130 may process the order with a separate medical test processing model that is appropriate for the patient's age or cancel the order.

In step 1006, the system 130 validates that the data values for the one or more medical tests satisfy all required fields of the medical test processing model. If not all the required fields of the medical test processing model have received data values, then the associated collector 406A may wait to receive all data values for all required fields before proceeding to run the medical test processing model.

In step 1008, the system 130 validates that the data values are valid values for the lookup value type of the medical test processing model. In some embodiments, each medical test in the medical test processing model may be restricted to certain valid value types. For example, data values for some medical tests may be required to text, numbers, positive/ negative, or so on. The system 130 may confirm that data values received from a medical test are valid value types.

In step 1010, the system 130 validates that the data values are within a required data value range of the medical test processing model. In some embodiments, each medical test in the medical test processing model may be restricted to a specific range of values, such as 0-100, 0-5, >0, <0, and so on. The system 130 may confirm that data values received from a medical test are in the required range.

In step 1012, the system validates that the data values are in the required units for the medical test processing model. In some embodiments, each medical test in the medical test processing model may be required to be in certain units (e.g., ng/mL). The system 130 may confirm that data values received from a medical test are in the required units.

In step 1014, when all validation tests are passed, the system 130 generates output text based on applying the interpretation rule, including data value criterion of the interpretation rule. If any of the validation tests are not passed, then the system 130 may cancel the order and transmit a cancellation message to the EHR 111 indicating that the order was cancelled.

FIG. 11 illustrates an exemplary generated interpretation text. Example 1100 corresponds to an order for interpretation of medical tests related to coagulation. One or more medical tests and corresponding data values 1102 are shown, including PT, INR, aPTT, Fibrinogen, Platelet, Factor VIII, vWF antigen (Ag), and vWF functional (RCF). The data criterion for one or more of the medical tests is a range criterion and the data criterion for other of the medical tests is a ratio. The system 130 generates interpretation text 1104 based on the medical test data values, where the interpretation text 1104 interprets the data values shown for diagnosis of the patient and development of a treatment plan.

Figure 12:
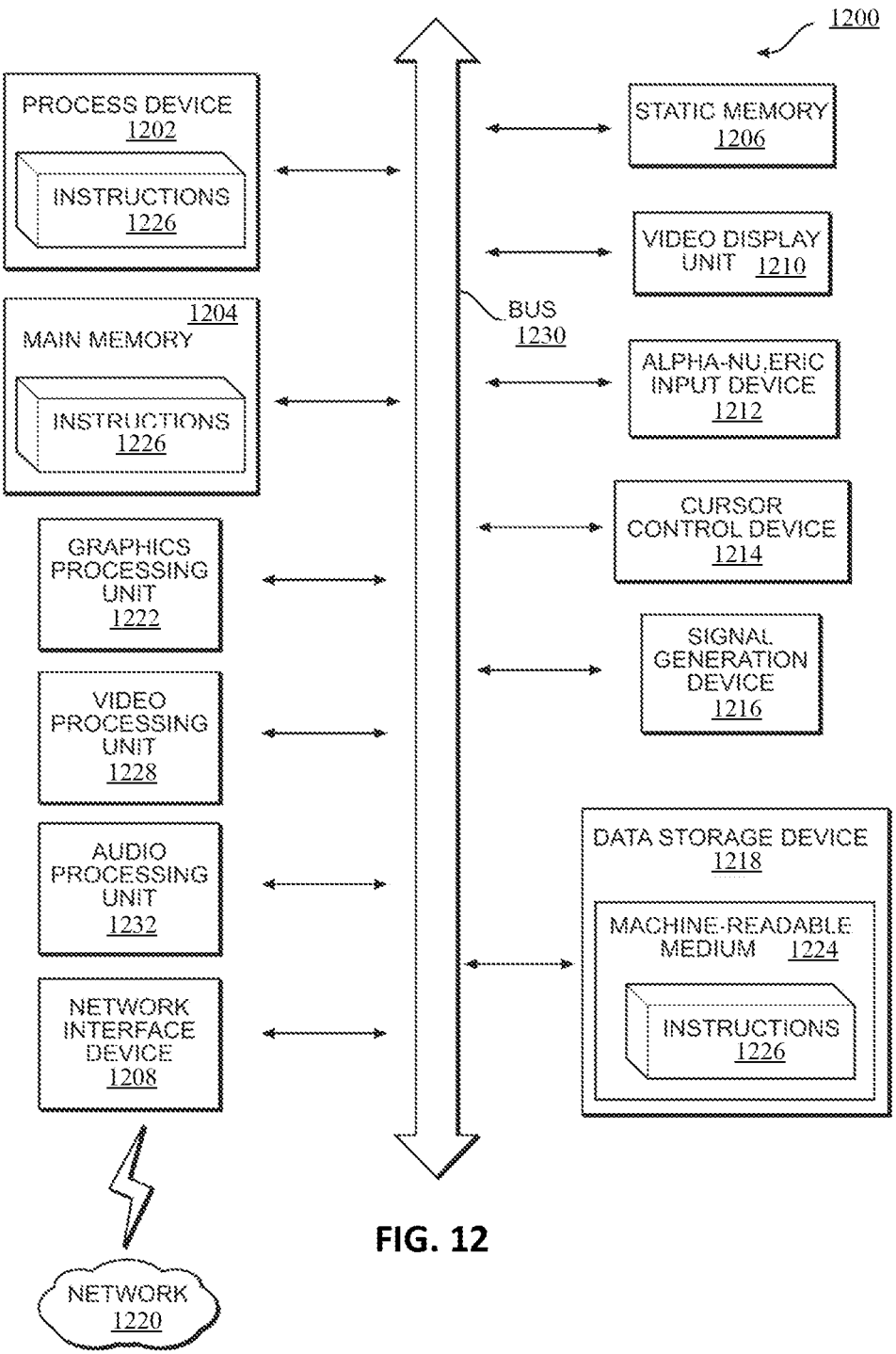
FIG. 12 illustrates an exemplary computer system wherein embodiments may be executed.

FIG. 12 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 1200 includes a processing device 1202, a main memory 1204 (e.g., read-only memory (ROM), flash memory, dynamic random access memory (DRAM) such as synchronous DRAM (SDRAM) or Rambus DRAM (RDRAM), etc.), a static memory 1206 (e.g., flash memory, static random access memory (SRAM), etc.), and a data storage device 1218, which communicate with each other via a bus 1230.

Processing device 1202 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. The processing device 1202 is configured to execute instructions 1226 for performing the operations and steps discussed herein.

The computer system 1200 may further include a network interface device 1208 to communicate over the network 1220. The computer system 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse) or an input touch device, a graphics processing unit 1222, a signal generation device 1216 (e.g., a speaker), graphics processing unit 1222, video processing unit 1228, and audio processing unit 1232.

The data storage device 1218 may include a machine-readable storage medium 1224 (also known as a computer-readable medium) on which is stored one or more sets of instructions or software 1226 embodying any one or more of the methodologies or functions described herein. The instructions 1226 may also reside, completely or at least partially, within the main memory 1204 and/or within the processing device 1202 during execution thereof by the computer system 1200, the main memory 1204 and the processing device 1202 also constituting machine-readable storage media.

In one implementation, the instructions 1226 include instructions to implement functionality corresponding to the components of a device to perform the disclosure herein. While the machine-readable storage medium 1224 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

In general, the terms "engine" and "module", as used herein, refer to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on one or more computer readable media, such as compact discs, digital video discs, flash drives, or any other tangible media. Such software code may be stored, partially or fully, on a memory device of the executing computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A system comprising one or more processors, and a non-transitory computer readable medium storing a plurality of instructions, which when executed, cause the one or more processors to perform the operations of:

receiving a plurality of data sets from one or more external computing systems, each of the data sets including multiple data fields including a source identifier, one or more code values and data values for one or more medical tests being associated with a patient identifier;

providing a plurality of medical test processing models wherein each medical test processing model includes a data interpretation rule structure for processing different types of the medical tests;

selecting a particular medical test processing model based on the one or more code values of the medical test;

creating, by a collector system, a collector, wherein the collector resides in a collector pool of multiple collectors, and wherein each collector of the multiple collectors asynchronously wait to receive medical data;

asynchronously waiting, by the collector, to receive one or more required data values for the selected medical test processing model from the one or more external computer systems, wherein the required data values are data that the collector requires for computation of the selected medical test processing model;

when the required subset of data values is received, using the selected medical test processing model, processing the data values of the one or more medical tests to generate an interpreted medical test data set, the interpreted data set including the source identifier, the one or more code values and data values for the one or more medical tests, and a set of interpretation text based on the medical test data values; and transmitting the interpreted medical test data set to an external computing system, wherein the external computing system is selected based on the source identifier.

2. The system of claim 1, wherein the plurality of instructions cause the one or more processors to further perform the operations of:

determining that a medical test processing model is valid for the age of the patient.

3. The system of claim 1, wherein the plurality of instructions cause the one or more processors to further perform the operations of:

selecting a medical test processing model for a particular medical test, wherein a different model is applicable based on the age of the patient.

4. The system of claim 1, wherein processing the data values of the one or more medical tests comprises:
providing a rules engine comprising multiple interpretation rules used to analyze the data values of the one or more values of a medical test, the interpretation rules including lookup data values;
selecting an interpretation rule based on the data values of the medical test and the lookup data values; and
generating an output of interpretation text where the interpretation rule includes lookup data values of the medical test corresponding to data value criterion of the interpretation rule.

5. The system of claim 4, wherein the data values for the medical test include two values, the first value being either a positive or a negative test result, and the second value being either a positive or a negative test result.

6. The system of claim 4, wherein the plurality of instructions cause the one or more processors to further perform the operations of:
receiving an order from the one or more external computer systems and creating, by the collector system, the collector;
in response to receiving a plurality of events from the one or more external computer systems, evaluating the events to determine a subset of events that match an order identifier and patient identifier of the collector; and
storing one or more data values for the one or more medical tests from the subset of events and analyzing the data values to determine that a required subset of data values is received.

7. The system of claim 1, wherein the plurality of instructions cause the one or more processors to further perform the operations of:
after generating an interpreted medical test data set, asynchronously waiting, by the collector, for new data values for additional medical tests;
iteratively generating new interpreted medical test data sets when new data values for additional medical tests are received by using the selected medical test processing model to process the new data values.

8. The system of claim 4, wherein the plurality of instructions cause the one or more processors to further perform the operations of:
providing a configuration mapping comprising a plurality of mappings from a first set of code values for the one or more medical tests, the first set of code values from the external computing systems, to a second set of code values for the one or more medical tests, the second set of code values for the interpretation rules;
prior to applying the interpretation rule, applying the configuration mapping to map the code values of the one or more medical tests of the data sets into the second set of code values.

9. The system of claim 8, wherein the plurality of instructions cause the one or more processors to further perform the operations of:
providing a model user interface for configuring one or more medical test processing models, the model user interface including user interface elements for adding one or more medical tests and data values to a medical test processing model;
providing a model installation user interface for configuring one or more configuration mappings, the model installation user interface including user interface elements for editing mapped code values of the one or more configuration mappings.

10. A computer-implemented method for data interpretation:
receiving a plurality of data sets from one or more external computing systems, each of the data sets including multiple data fields including a source identifier, one or more code values and data values for one or more medical tests being associated with a patient identifier;
providing a plurality of medical test processing models wherein each medical test processing model includes a data interpretation rule structure for processing different types of the medical tests;
selecting a particular medical test processing model based on the one or more code values of the medical test;
creating, by a collector system, a collector, wherein the collector resides in a collector pool of multiple collectors, and wherein each collector of the multiple collectors asynchronously wait to receive medical data;
asynchronously waiting, by the collector, to receive one or more required data values for the selected medical test processing model from the one or more external computer systems, wherein the required data values are data that the
when the required subset of data values is received, using the selected medical test processing model, processing the data values of the one or more medical tests to generate an interpreted medical test data set, the interpreted data set including the source identifier, the one or more code values and data values for the one or more medical tests, and a set of interpretation text based on the medical test data values; and
transmitting the interpreted medical test data set to an external computing system, wherein the external computing system is selected based on the source identifier.

11. The method of claim 10, further comprising:
determining that a medical test processing model is valid for the age of the patient.

12. The method of claim 10, further comprising:
selecting a medical test processing model for a particular medical test, wherein a different model is applicable based on the age of the patient.

13. The method of claim 10, further comprising:
providing a rules engine comprising multiple interpretation rules used to analyze the data values of the one or more values of a medical test, the interpretation rules including lookup data values;
selecting an interpretation rule based on the data values of the medical test and the lookup data values; and
generating an output of interpretation text where the interpretation rule includes lookup data values of the medical test corresponding to data value criterion of the interpretation rule.

14. The method of claim 13, wherein the data values for the medical test include two values, the first value being either a positive or a negative test result, and the second value being either a positive or a negative test result.

15. The method of claim 13, further comprising:
receiving an order from the one or more external computer systems and creating, by the collector system, the collector;
in response to receiving a plurality of events from the one or more external computer systems, evaluating the events to determine a subset of events that match an order identifier and patient identifier of the collector; and storing one or more data values for the one or more medical tests from the subset of events and analyzing the data values to determine that a required subset of data values is received.

16. The method of claim 15, further comprising:

after generating an interpreted medical test data set, asynchronously waiting, by the collector, for new data values for additional medical tests;

iteratively generating new interpreted medical test data sets when new data values for additional medical tests are received by using the selected medical test processing model to process the new data values.

17. The method of claim 13, further comprising:

providing a configuration mapping comprising a plurality of mappings from a first set of code values for the one or more medical tests, the first set of code values from the external computing systems, to a second set of code values for the one or more medical tests, the second set of code values for the interpretation rules;

prior to applying the interpretation rule, applying the configuration mapping to map the code values of the one or more medical tests of the data sets into the second set of code values.

18. The method of claim 17, further comprising:

providing a model user interface for configuring one or more medical test processing models, the model user interface including user interface elements for adding one or more medical tests and data values to a medical test processing model;

providing a model installation user interface for configuring one or more configuration mappings, the model installation user interface including user interface elements for editing mapped code values of the one or more configuration mappings.

19. The system of claim 1, wherein the plurality of instructions cause the one or more processors to further perform the operations of:

receiving by a job scheduler a request from the collector to schedule a job for processing a medical text processing model;

adding the job to a job pool;

performing the job to process the medical text processing model using the required subset of data values to generate the interpreted medical test data set.

20. The method of claim 10, further comprising:

receiving by a job scheduler a request from the collector to schedule a job for processing a medical text processing model;

adding the job to a job pool;

performing the job to process the medical text processing model using the required subset of data values to generate the interpreted medical test data set.

21. The system of claim 1, wherein the plurality of instructions cause the one or more processors to further perform the operations of:

changing a status of the collector from a waiting status to a ready status when required medical test data values are received to allow processing of the selected medical test processing model.

22. The method of claim 10, further comprising:

changing a status of the collector from a waiting status to a ready status when required medical test data values are received to allow processing of the selected medical test processing model.

* * * * *